(12) United States Patent
Ise et al.

(10) Patent No.: US 7,732,606 B2
(45) Date of Patent: *Jun. 8, 2010

(54) LIGHT-EMITTING DEVICE

(75) Inventors: Toshihiro Ise, Minami-ashigara (JP);
Satoshi Sano, Minami-ashigara (JP);
Tatsuya Igarashi, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 1032 days.

This patent is subject to a terminal disclaimer.

(21) Appl. No.: 11/234,141

(22) Filed: Sep. 26, 2005

(65) Prior Publication Data

US 2006/0073359 A1 Apr. 6, 2006

(30) Foreign Application Priority Data

Sep. 27, 2004 (JP) ............................. 2004-279153

(51) Int. Cl.
C09K 11/06 (2006.01)
C07D 213/02 (2006.01)
H01L 51/54 (2006.01)

(52) U.S. Cl. ........................... 546/4; 428/917; 313/504; 257/E51.044

(58) Field of Classification Search ........................ None
See application file for complete search history.

(56) References Cited

U.S. PATENT DOCUMENTS

| | | | |
|---|---|---|---|
| 6,303,231 B1 | 10/2001 | Sawada et al. | |
| 6,303,238 B1 | 10/2001 | Thompson et al. | |
| 6,653,654 B1 | 11/2003 | Che | |
| 7,442,797 B2 * | 10/2008 | Itoh et al. ........................ | 546/6 |
| 7,569,692 B2 | 8/2009 | Nii et al. | |
| 2002/0008233 A1 | 1/2002 | Forrest et al. | |
| 2002/0013306 A1 | 1/2002 | Lowe | |
| 2002/0068190 A1 | 6/2002 | Tsuboyama et al. | |
| 2003/0205707 A1 | 11/2003 | Chi-Ming | |
| 2005/0123788 A1 | 6/2005 | Huo et al. | |
| 2005/0170206 A1 | 8/2005 | Ma et al. | |
| 2005/0170209 A1 | 8/2005 | Lee et al. | |
| 2006/0073359 A1 | 4/2006 | Ise et al. | |
| 2006/0134460 A1 | 6/2006 | Kondakova et al. | |
| 2006/0134461 A1 * | 6/2006 | Huo et al. .................... | 428/690 |
| 2006/0182992 A1 * | 8/2006 | Nii et al. ..................... | 428/690 |
| 2006/0264625 A1 | 11/2006 | Nakayama et al. | |
| 2006/0286406 A1 | 12/2006 | Igarashi et al. | |
| 2007/0082284 A1 * | 4/2007 | Stoessel et al. ................ | 430/84 |
| 2007/0103060 A1 | 5/2007 | Itoh et al. | |
| 2008/0001530 A1 * | 1/2008 | Ise et al. ...................... | 313/504 |
| 2008/0036373 A1 | 2/2008 | Itoh et al. | |
| 2009/0128008 A1 | 5/2009 | Ise et al. | |

FOREIGN PATENT DOCUMENTS

| | | |
|---|---|---|
| EP | 0 969 532 A2 | 1/2000 |
| JP | 5-9470 A | 1/1993 |
| JP | 2000-048960 A | 2/2000 |
| JP | 2001-338768 A | 12/2001 |
| JP | 2002-175884 A | 6/2002 |
| JP | 2002-305083 A | 10/2002 |
| JP | 2002-363552 A | 12/2002 |
| JP | 2003-68466 A | 3/2003 |
| JP | 2003-77674 A | 3/2003 |
| JP | 2003-123976 A | 4/2003 |
| JP | 2003-123981 A | 4/2003 |
| JP | 2004-331508 A | 11/2004 |
| JP | 2005-220136 A | 8/2005 |
| JP | 2005-310733 A | 11/2005 |
| JP | 2006-093542 A | 4/2006 |
| JP | 2006-120811 A | 5/2006 |
| JP | 2006-256999 A | 9/2006 |
| JP | 2006-261623 A | 9/2006 |
| JP | 2006-332620 A | 12/2006 |
| JP | 2007-019462 A | 1/2007 |
| JP | 2007-073845 A | 3/2007 |
| JP | 2008-037848 A | 2/2008 |
| JP | 2008-103535 A | 5/2008 |
| WO | WO-00/57676 A1 | 9/2000 |
| WO | WO-2003/093283 A1 | 11/2003 |
| WO | WO-2004-039914 A1 | 5/2004 |

(Continued)

OTHER PUBLICATIONS

Japanese Office Action and Translation Issued in corresponding Japanese Application No. 2004-279153 (dated Nov. 11, 2009).

(Continued)

*Primary Examiner*—Marie R. Yamnitzky
(74) *Attorney, Agent, or Firm*—Birch, Stewart, Kolasch & Birch, LLP

(57) ABSTRACT

An organic electroluminescent device having a pair of electrodes and at least one organic layer including a light-emitting layer interposed between the pair of electrodes, in which the organic layer contains at least one platinum complex compound having a quadridentate ligand containing a partial structure represented by formula (I):

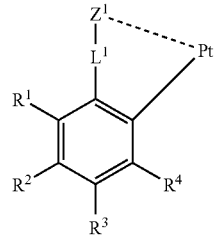

Formula (I)

wherein $Z^1$ represents a nitrogen-containing heterocycle coordinated to the platinum through a nitrogen atom; $L^1$ represents a single bond or a linking group; $R^1$, $R^3$ and $R^4$ each independently represent a hydrogen atom or a substituent; and $R^2$ represents a substituent.

2 Claims, No Drawings

FOREIGN PATENT DOCUMENTS

| WO | WO 2004/108857 | A1 | * | 12/2004 |
| WO | WO-2005/042444 | A1 | | 5/2005 |
| WO | WO 2005/042444 | A2 | * | 5/2005 |
| WO | WO 2005/042550 | A1 | * | 5/2005 |
| WO | WO 2006/033440 | A1 | * | 3/2006 |

OTHER PUBLICATIONS

Nature 395, pp. 151-154, Baldo et al. (1998).
Chem. Eur. J. 9(6), pp. 1263-1272, Che et al. (2003).

* cited by examiner

LIGHT-EMITTING DEVICE

FIELD OF THE INVENTION

The present invention relates to an organic electroluminescent device (hereinafter, referred to also as "organic EL device," "light-emitting device," or "device"). In particular, the present invention relates to an organic electroluminescent device excellent in emitting characteristics and durability.

BACKGROUND OF THE INVENTION

Energetic studies and developments are being made as to organic electroluminescent devices (organic EL devices), because highly luminescent emission is obtained from these devices with low-voltage driving. Generally, the organic EL devices are constituted of an organic layer including a light-emitting layer, and a pair of electrodes between which the organic layer is sandwiched. In such devices, electrons injected from the cathode are recombined with holes injected from the anode in the light-emitting layer, to produce excitons, whose energy is utilized to emit light.

Improvement in the efficiency of devices has been recently made by using a phosphorescence-emitting material. Iridium complexes, platinum complexes, and the like are such a phosphorescence-emitting material (see, for example, U.S. Pat. No. 6,303,238 and WO 00/57676). However, devices having both high efficiency and high durability have not been developed. There has been a need for development of phosphorescent materials capable of satisfying both.

SUMMARY OF THE INVENTION

The present invention resides in an organic electroluminescent device having a pair of electrodes and at least one organic layer including a light-emitting layer interposed between the pair of electrodes, in which the organic layer contains at least one platinum complex compound having a quadridentate ligand containing a partial structure represented by formula (I):

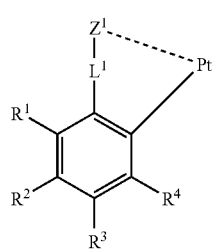

Formula (I)

wherein $Z^1$ represents a nitrogen-containing heterocycle coordinated to the platinum through a nitrogen atom; $L^1$ represents a single bond or a linking group; $R^1$, $R^3$ and $R^4$ each independently represent a hydrogen atom or a substituent; and $R^2$ represents a substituent.

Further, the present invention resides in a compound represented by formula (V):

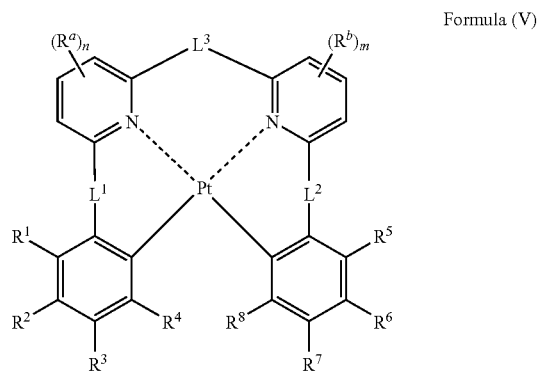

Formula (V)

wherein $L^1$, $L^2$ and $L^3$ each independently represent a single bond or a linking group; $R^1$, $R^3$, $R^4$, $R^5$, $R^7$ and $R^8$ each independently represent a hydrogen atom or a substituent; $R^2$ and $R^6$ each independently represent a substituent; $R^a$ and $R^b$ each independently represent a substituent; and n and m each independently represent an integer of from 0 to 3.

Other and further features and advantages of the invention will appear more fully from the following description.

DETAILED DESCRIPTION OF THE INVENTION

According to the present invention, there is provided the following means:

(1) An organic electroluminescent device having a pair of electrodes and at least one organic layer including a light-emitting layer interposed between the pair of electrodes, wherein the organic layer contains at least one platinum complex compound having a quadridentate ligand containing a partial structure represented by formula (I):

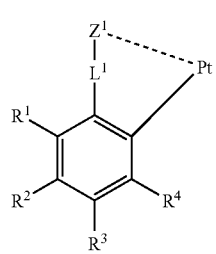

Formula (I)

wherein $Z^1$ represents a nitrogen-containing heterocycle coordinated to the platinum through a nitrogen atom; $L^1$ represents a single bond or a linking group; $R^1$, $R^3$ and $R^4$ each independently represent a hydrogen atom or a substituent; and $R^2$ represents a substituent.

(2) The organic electroluminescent device according to the above item (1), wherein the platinum complex compound having a quadridentate ligand containing a partial structure represented by formula (I) is a platinum complex compound represented by formula (II):

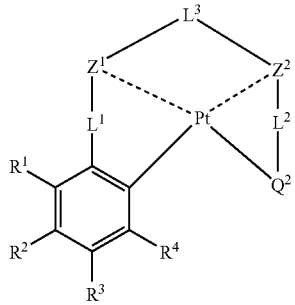

Formula (II)

wherein $Z^1$ and $Z^2$ each independently represent a nitrogen-containing heterocycle coordinated to the platinum through a nitrogen atom; $Q^2$ represents a group bonded to the platinum through a carbon atom, an oxygen atom, a sulfur atom, a nitrogen atom or a phosphorous atom; $L^1$, $L^2$ and $L^3$ each independently represent a single bond or a linking group; $R^1$, $R^3$ and $R^4$ each independently represent a hydrogen atom or a substituent; and $R^2$ represents a substituent.

(3) The organic electroluminescent device according to the above item (2), wherein the platinum complex compound represented by formula (II) is a platinum complex compound represented by formula (III):

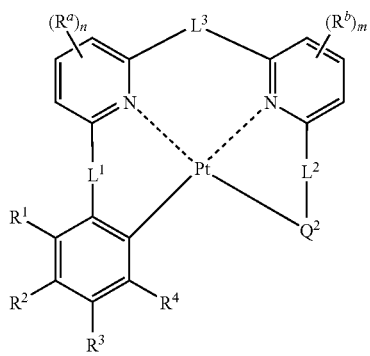

Formula (III)

wherein $Q^2$ represents a group bonded to the platinum through a carbon atom, an oxygen atom, a sulfur atom, a nitrogen atom or a phosphorous atom; $L^1$, $L^2$ and $L^3$ each independently represent a single bond or a linking group; $R^1$, $R^3$ and $R^4$ each independently represent a hydrogen atom or a substituent; $R^2$ represents a substituent; $R^a$ and $R^b$ each independently represent a substituent; and n and m each independently represent an integer of from 0 to 3.

(4) The organic electroluminescent device according to the above item (3), wherein the platinum complex compound represented by formula (III) is a platinum complex compound represented by formula (IV):

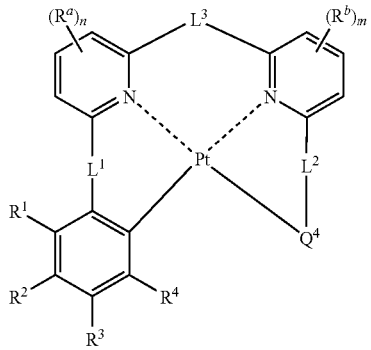

Formula (IV)

wherein $Q^4$ represents an aromatic hydrocarbon group or an aromatic heterocyclic group, each bonded to the platinum through a carbon atom or a nitrogen atom; $L^1$, $L^2$ and $L^3$ each independently represent a single bond or a linking group; $R^1$, $R^3$ and $R^4$ each independently represent a hydrogen atom or a substituent; $R^2$ represents a substituent; $R^a$ and $R^b$ each independently represent a substituent; and n and m each independently represent an integer of from 0 to 3.

(5) The organic electroluminescent device according to the above item (1), wherein the platinum complex compound having a quadridentate ligand containing a partial structure represented by formula (I) is a compound represented by formula (V):

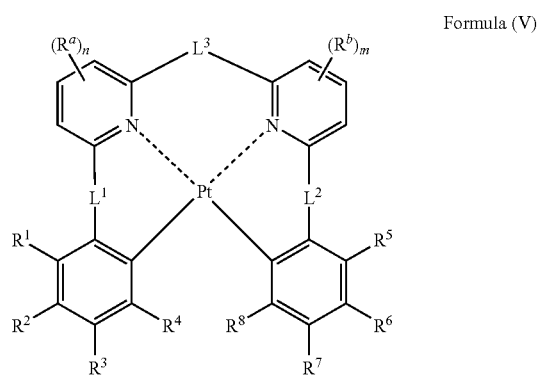

Formula (V)

wherein $L^1$, $L^2$ and $L^3$ each independently represent a single bond or a linking group; $R^1$, $R^3$, $R^4$, $R^5$, $R^7$ and $R^8$ each independently represent a hydrogen atom or a substituent; $R^2$ and $R^6$ each independently represent a substituent; $R^a$ and $R^b$ each independently represent a substituent; and n and m each independently represent an integer of from 0 to 3.

(6) The organic electroluminescent device according to any one of the above items (1) to (5), wherein at least one of the platinum complex compound having a quadridentate ligand containing a partial structure represented by formula (I) or the compound represented by any one of formulae (II) to (V) is contained in the light-emitting layer.

(7) The organic electroluminescent device according to any one of the above items (1) to (6), wherein at least one of the platinum complex compound having a quadridentate ligand containing a partial structure represented by formula (I) or the compound represented by any one of formulae (II) to (V), and at least one host material are contained in the light-emitting layer.

(8) A compound represented by formula (V):

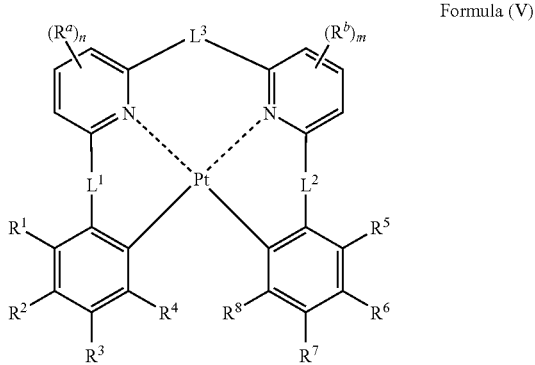

Formula (V)

wherein $L^1$, $L^2$ and $L^3$ each independently represent a single bond or a linking group; $R^1$, $R^3$, $R^4$, $R^5$, $R^7$ and $R^8$ each independently represent a hydrogen atom or a substituent; $R^2$ and $R^6$ each independently represent a substituent; $R^a$ and $R^b$ each independently represent a substituent; and n and m each independently represent an integer of from 0 to 3.

The organic EL device of the present invention will be described in detail hereinbelow.

The organic EL device of the present invention has a pair of electrodes and at least one organic layer including a light-emitting layer interposed between the pair of electrodes. The organic EL device of the present invention comprises, in the organic layer, a platinum complex having a quadridentate ligand and a substituent at the para-position of the phenyl group bonded to platinum. The aforementioned bond of the carbon atom of the phenyl group to the platinum is usually a covalent bond, and the bonds of other atoms to the platinum are respectively a coordinate bond or a covalent bond.

Besides the light-emitting layer, a hole-injecting layer, a hole-transporting layer, an electron-injecting layer, an electron-transporting layer, a hole-blocking layer, an electron-blocking layer, an exciton-blocking layer, a protective layer and the like may be appropriately disposed in the organic EL device of the present invention. Also, each of these layers may be provided with other functions.

The platinum complex compound having a quadridentate ligand containing a partial structure represented by formula (I) and the compound represented by any one of formulae (II) to (V) are not limited in their functions, and may be contained in any layer when the organic layer is constituted of plural layers. They are preferably contained in the light-emitting layer, more preferably contained as a light-emitting material in the light-emitting layer, and particularly preferably contained together with at least one host material in the light-emitting layer.

When the platinum complex for use in the present invention is contained as a light-emitting material in the light-emitting layer, the content of the platinum complex is preferably 0.1 mass % or more and 50 mass % or less, more preferably 0.2 mass % or more and 30 mass % or less, still more preferably 0.3 mass % or more and 20 mass % or less, and most preferably 0.5 mass % or more and 10 mass % or less, based on the whole mass of the said layer.

The host material is a compound that serves to inject and carry charges primarily in the light-emitting layer, and does not itself substantially emit light. The term "the host material does not substantially emit light" in this specification means that the amount of light emitted from the compound which does not substantially emit light is preferably 5% or less, more preferably 3% or less, and still more preferably 1% or less, based on the total amount of light emitted from the whole device.

Although no particular limitation is imposed on the concentration of the host material in the light-emitting layer, the host material is preferably a major component in the light-emitting layer (that is, the host material is a component contained in the largest amount). The amount of the host material is preferably 50 mass % or more and 99.9 mass % or less, still more preferably 70 mass % or more and 99.8 mass % or less, particularly preferably 80 mass % or more and 99.7 mass % or less and most preferably 90 mass % or more and 99.5 mass % or less.

The glass transition point of the host material is preferably 100° C. or more and 500° C. or less, more preferably 110° C. or more and 300° C. or less, and still more preferably 120° C. or more and 250° C. or less.

In the present invention, the fluorescent wavelength of the host material put in a film state and contained in the light-emitting layer is preferably 400 nm or more and 650 nm or less, more preferably 420 nm or more and 600 nm or less, and most preferably 440 nm or more and 550 nm or less.

As the host material that can be used in the present invention, compounds as described in paragraph Nos. [0113] to [0161] of JP-A-2002-100476 ("JP-A" means unexamined published Japanese patent application), and compounds as described in paragraph Nos. [0087] to [0098] of JP-A-2004-214179 may be preferably used. However, the present invention is not limited to these compounds.

The platinum complex that can be used in the present invention is preferably a phosphorescent material.

The phosphorescence lifetime (at a room temperature) of the platinum complex that can be used in the present invention is preferably 1 ms or less, more preferably 100 μs or less, and still more preferably 10 μs or less, though there is no particular limitation to the lifetime. The phosphorescence quantum yield of the complex at a room temperature is preferably 70% or more, more preferably 80% or more, and still more preferably 90% or more.

In the organic EL device of the present invention, it is preferable that each $T_1$ value (energy value in a lowest triplet excited state) of the host material and the light-emitting material is 60 kcal/mol (251 kJ/mol) or more, and that $\lambda_{max}$ (emission maximum wavelength) of phosphorescence obtained from the phosphorescent compound is preferably 550 nm or less; it is more preferable that each $T_1$ value of the host material and the light-emitting material is 62 kcal/mol (259 kJ/mol) or more, and that $\lambda_{max}$ (emission maximum wavelength) of phosphorescence obtained from the light-emitting material is preferably 500 nm or less; and it is still more preferable that each $T_1$ value of the host material and the light-emitting material is 65 kcal/mol (272 kJ/mol) or more, and that $\lambda_{max}$ (emission maximum wavelength) of phosphorescence obtained from the light-emitting material is preferably 480 nm or less.

In the organic EL device of the present invention, $T_1$ value of an organic layer adjacent to the light-emitting layer is preferably 60 kcal/mol or more, more preferably 63 kcal/mol or more, and still more preferably 65 kcal/mol or more.

In the organic EL device of the present invention, the organic compound layer comprises at least three layers including a hole-transporting layer, a light-emitting layer and an electron-transporting layer. The electron-transporting layer has an Ip value of preferably 5.9 eV or more, more preferably 6.0 eV or more, and still more preferably 6.1 eV or more.

The platinum complex compound having a quadridentate ligand containing a partial structure represented by formula (I) is described below.

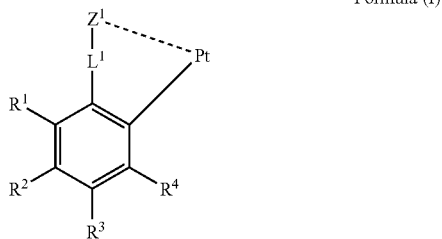

Formula (I)

In formula (I), $Z^1$ represents a nitrogen-containing heterocycle coordinated to the platinum through a nitrogen atom; $L^1$ represents a single bond or a linking group; $R^1$, $R^3$ and $R^4$ each independently represent a hydrogen atom or a substituent; and $R^2$ represents a substituent.

$Z^1$ represents a nitrogen-containing heterocycle coordinated to the platinum through a nitrogen atom. Examples of $Z^1$ include a pyridine ring, pyrazine ring, pyrimidine ring, pyridazine ring, triazine ring, pyrazole ring, imidazole ring, oxazole ring, thiazole ring, triazole ring, oxadiazole ring, thiadiazole ring, and benzo-condensed or pyrido-condensed rings of these compounds. Among these compounds, a pyridine ring, pyrazine ring, pyrimidine ring, pyrazole ring and triazole ring are preferable; a pyridine ring, pyrazine ring, and pyrimidine ring are more preferable; and a pyridine ring is particularly preferable. These compounds may have a substituent. As the substituent, those given as the examples of the substituent of $L^1$, which will be explained later, can be applied.

$L^1$ represents a single bond or a linking group. The linking group is preferably, though not limited to, a linking group comprising a carbon atom, a nitrogen atom, an oxygen atom, a sulfur atom or a silicon atom. Specific examples of the linking group are shown below. However, the present invention is not limited to these examples.

Linking Group

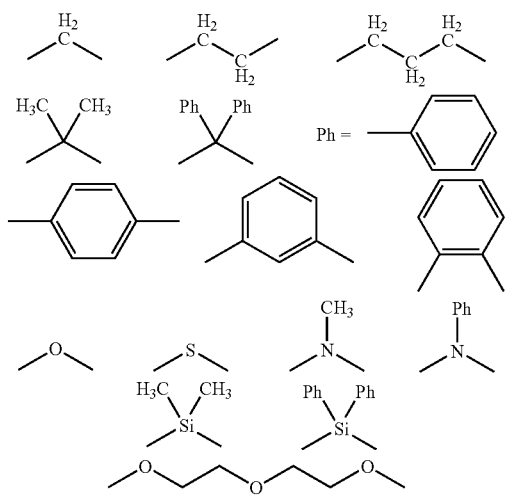

These linking groups may have a substituent, if possible. Examples of the substituent that can be introduced into the linking groups include an alkyl group (preferably an alkyl group having from 1 to 30 carbon atoms, more preferably from 1 to 20 carbon atoms, and particularly preferably from 1 to 10 carbon atoms, e.g., methyl, ethyl, isopropyl, tert-butyl, n-octyl, n-decyl, n-hexadecyl, cyclopropyl, cyclopentyl, and cyclohexyl), an alkenyl group (preferably an alkenyl group having from 2 to 30 carbon atoms, more preferably from 2 to 20 carbon atoms, and particularly preferably from 2 to 10 carbon atoms, e.g., vinyl, allyl, 2-butenyl, and 3-pentenyl), an alkynyl group (preferably an alkynyl group having from 2 to 30 carbon atoms, more preferably from 2 to 20 carbon atoms, and particularly preferably from 2 to 10 carbon atoms, e.g., propargyl, and 3-pentynyl), an aryl group (preferably an aryl group having from 6 to 30 carbon atoms, more preferably from 6 to 20 carbon atoms, and particularly preferably from 6 to 12 carbon atoms, e.g., phenyl, p-methylphenyl, naphthyl, and anthranyl), an amino group (preferably an amino group having from 0 to 30 carbon atoms, more preferably from 0 to 20 carbon atoms, and particularly preferably from 0 to 10 carbon atoms, e.g., amino, methylamino, dimethylamino, diethylamino, dibenzylamino, diphenylamino, and ditolylamno), an alkoxy group (preferably an alkoxy group having from 1 to 30 carbon atoms, more preferably from 1 to 20 carbon atoms, and particularly preferably from 1 to 10 carbon atoms, e.g., methoxy, ethoxy, butoxy, and 2-ethylhexyloxy), an aryloxy group (preferably an aryloxy group having from 6 to 30 carbon atoms, more preferably from 6 to 20 carbon atoms, and particularly preferably from 6 to 12 carbon atoms, e.g., phenyloxy, 1-naphthyloxy, and 2-naphthyloxy), a heterocyclic oxy group (a heterocyclic oxy group having preferably 1 to 30 carbon atoms, more preferably 1 to 20 carbon atoms, and particularly preferably 1 to 12 carbon atoms, e.g., pyridyloxy, pyrazyloxy, pyrimidyloxy, and quinolyloxy), an acyl group (preferably an acyl group having from 1 to 30 carbon atoms, more preferably from 1 to 20 carbon atoms, and particularly preferably from 1 to 12 carbon atoms, e.g., acetyl, benzoyl, formyl, and pivaloyl), an alkoxycarbonyl group (preferably an alkoxycarbonyl group having from 2 to 30 carbon atoms, more preferably from 2 to 20 carbon atoms, and particularly preferably from 2 to 12 carbon atoms, e.g., methoxycarbonyl, and ethoxycarbonyl), an aryloxycarbonyl group (preferably an aryloxycarbonyl group having from 7 to 30 carbon atoms, more preferably from 7 to 20 carbon atoms, and particularly preferably from 7 to 12 carbon atoms, e.g., phenyloxycarbonyl), an acyloxy group (preferably an acyloxy group having from 2 to 30 carbon atoms, more preferably from 2 to 20 carbon atoms, and particularly preferably from 2 to 10 carbon atoms, e.g., acetoxy, and benzoyloxy), an acylamino group (preferably an acylamino group having from 2 to 30 carbon atoms, more preferably from 2 to 20 carbon atoms, and particularly preferably from 2 to 10 carbon atoms, e.g., acetylamino, and benzoylamino), an alkoxycarbonylamino group (preferably an alkoxycarbonylamino group having from 2 to 30 carbon atoms, more preferably from 2 to 20 carbon atoms, and particularly preferably from 2 to 12 carbon atoms, e.g., methoxycarbonylamino), an aryloxycarbonylamino group (preferably an aryloxycarbonylamino group having from 7 to 30 carbon atoms, more preferably from 7 to 20 carbon atoms, and particularly preferably from 7 to 12 carbon atoms, e.g., phenyloxycarbonylamino), a sulfonylamino group (preferably a sulfonylamino group having from 1 to 30 carbon atoms, more preferably from 1 to 20 carbon atoms, and particularly preferably from 1 to 12 carbon atoms, e.g., methanesulfonylamino, and benzenesulfonylamino), a sulfamoyl group (preferably a sulfamoyl group having from 0 to 30 carbon atoms, more preferably from 0 to 20 carbon atoms, and particularly preferably from 0 to 12 carbon atoms, e.g., sulfamoyl, methylsulfamoyl, dimethylsulfamoyl, and phenylsulfamoyl), a carbamoyl group (preferably a carbamoyl group having from 1 to 30 carbon atoms, more preferably from 1 to 20 carbon atoms, and particularly preferably from 1 to 12 carbon atoms, e.g., carbamoyl, methylcarbamoyl, diethylcarbamoyl, and phenylcarbamoyl), an alkylthio group (preferably an alkylthio group having from 1 to 30 carbon atoms, more preferably from 1 to 20 carbon atoms, and particularly preferably from 1 to 12 carbon atoms, e.g., methylthio, and ethylthio), an arylthio group (preferably an arylthio group having from 6 to 30 carbon atoms, more preferably from 6 to 20 carbon atoms, and particularly preferably from 6 to 12 carbon atoms, e.g., phenylthio), a heterocyclic thio group (preferably a heterocyclic thio group having 1 to 30 carbon atoms, more preferably 1 to 20 carbon atoms, and particularly preferably 1 to 12 carbon atoms, e.g., pyridylthio, 2-benzimidazolylthio, 2-benzoxazolylthio, and 2-benzthiazolylthio), a sulfonyl group (preferably a sulfonyl group having 1 to 30 carbon atoms, more preferably 1 to 20 carbon atoms, and particularly preferably 1 to 12 carbon atoms, e.g., mesyl, and tosyl), a sulfinyl group (preferably a sulfinyl group having 1 to 30 carbon atoms, more preferably 1 to 20 carbon atoms, and particularly preferably 1 to 12 carbon atoms, e.g., methanesulfinyl, and benzenesulfinyl), a ureido group (preferably a ureido group having 1 to 30 carbon atoms, more preferably 1 to 20 carbon atoms, and particularly preferably 1 to 12 carbon atoms, e.g., ureido, methylureido, and phenylureido), a phosphoric acid amido group (preferably a phosphoric acid amido group having 1 to 30 carbon atoms, more preferably 1 to 20 carbon atoms, and particularly preferably 1 to 12 carbon atoms, e.g., diethylphosphoric acid amido, and phenylphosphoric acid amido), a hydroxy group, a mercapto group, a halogen atom (e.g., fluorine, chlorine, bromine, and iodine atoms), a cyano group, a sulfo group, a carboxyl group, a nitro group, a hydroxamic acid group, a sulfino group, a hydrazino group, an imino group, a heterocyclic group (preferably a heterocyclic group having 1 to 30 carbon atoms, and more preferably 1 to 12 carbon atoms; as hetero atoms, e.g., nitrogen, oxygen, and sulfur atoms, and specifically, e.g., imidazolyl, pyridyl, quinolyl, furyl, thienyl, piperidyl, morpholino, benzoxazolyl, benzimidazolyl, benzthiazolyl, carbazolyl, and azevinyl), a silyl group (preferably a silyl group having 3 to 40 carbon atoms, more preferably 3 to 30 carbon atoms, and particularly preferably 3 to 24 carbon atoms, e.g., trimethylsilyl, and triphenylsilyl) and a silyloxy group (preferably a silyloxy group having 3 to 40 carbon atoms, more preferably 3 to 30 carbon atoms, and particularly preferably 3 to 24 carbon atoms, e.g., trimethylsilyloxy, and triphenylsilyloxy). These substituents may further be substituted. As the substituent, an alkyl group, an aryl group, a heterocyclic group, a halogen atom and a silyl group are preferable; an alkyl group, an aryl group, a heterocyclic group and a halogen atom are more preferable; and an alkyl group, an aryl group, an aromatic heterocyclic group and a fluorine atom are still more preferable.

$L^1$ is preferably a single bond, methylene group, dimethylmethylene group or diphenylmethylene group.

$R^1$, $R^3$ and $R^4$ each independently represent a hydrogen atom or a substituent. When $R^1$, $R^3$ and $R^4$ each represent a substituent, those given as the examples of the substituent of the linking group $L^1$ can be applied as the substituent. Preferable examples of $R^1$, $R^3$ or $R^4$ include a hydrogen atom, an alkyl group, an aryl group, an amino group, an alkoxy group, an aryloxy group, a heterocyclic oxy group, an acyl group, an alkoxycarbonyl group, an aryloxycarbonyl group, an alkylthio group, an arylthio group, a heterocyclic thio group, a sulfonyl group, a halogen atom, a cyano group, a heterocyclic group, a silyl group and a silyloxy group. More preferable examples of $R^1$, $R^3$ and $R^4$ include a hydrogen atom, an alkyl group, an aryl group, an amino group, an alkoxy group, an acyl group, an alkylthio group, a sulfonyl group, a halogen atom, a cyano group, a heterocyclic group and a silyl group. Still more preferable examples of $R^1$, $R^3$ and $R^4$ include a hydrogen atom, an alkyl group, an aryl group, an alkoxy group, an acyl group, a sulfonyl group, a fluorine atom, a cyano group, a heterocyclic group and a silyl group. Even more preferable examples of $R^1$, $R^3$ and $R^4$ include a hydrogen atom, an alkyl group, an aryl group, a sulfonyl group, a fluorine atom, a cyano group and a heterocyclic group. Particularly preferable examples of $R^1$, $R^3$ and $R^4$ include a hydrogen atom, an alkyl group, an aryl group, a fluorine atom, a cyano group and a heterocyclic group. Most preferable examples of $R^1$, $R^3$ and $R^4$ include a hydrogen atom, an alkyl group, a fluorine atom, a fluoroalkyl group and a cyano group. These substituents may be further substituted with a substituent.

$R^2$ represents a substituent. As the substituent represented by $R^2$, those given as the examples of the substituent represented by $R^1$, $R^3$ or $R^4$ can be applied. Preferable examples of the substituent represented by $R^2$ include an alkyl group, an aryl group, an amino group, an alkoxy group, an aryloxy group, a heterocyclic oxy group, an acyl group, an alkoxycarbonyl group, an aryloxycarbonyl group, an alkylthio group, an arylthio group, a heterocyclic thio group, a sulfonyl group, a halogen atom, a cyano group, a heterocyclic group, a silyl group and a silyloxy group. More preferable examples of the substituent represented by $R^2$ include an alkyl group, an aryl group, an amino group, an alkoxy group, an acyl group, an alkylthio group, a sulfonyl group, a halogen atom, a cyano group, a heterocyclic group and a silyl group. Still more preferable examples of the substituent represented by $R^2$ include an alkyl group, an aryl group, an alkoxy group, an acyl group, a sulfonyl group, a fluorine atom, a cyano group, a heterocyclic group and a silyl group. Even more preferable examples of the substituent represented by $R^2$ include an alkyl group, an aryl group, a sulfonyl group, a fluorine atom, a cyano group and a heterocyclic group. Particularly preferable examples of the substituent represented by $R^2$ include an alkyl group, an aryl group, a fluorine atom, a cyano group and a heterocyclic group. Most preferable examples of $R^2$ include an alkyl group, a fluorine atom, a fluoroalkyl group and a cyano group. These substituents may be further substituted with a substituent.

The platinum complex compound having a quadridentate ligand containing a partial structure represented by formula (I) is preferably a platinum complex represented by formula (II):

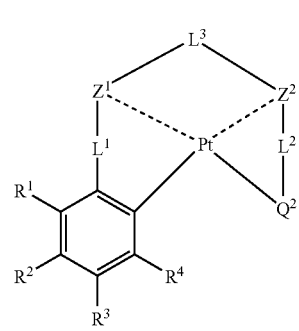

Formula (II)

In formula (II), $Z^1$ and $Z^2$ each independently represent a nitrogen-containing heterocycle coordinated to the platinum through a nitrogen atom. $Q^2$ represents a group bonded to the platinum through a carbon atom, an oxygen atom, a sulfur atom, a nitrogen atom or a phosphorous atom. $L^1$, $L^2$ and $L^3$ each independently represent a single bond or a linking group. $R^1$, $R^3$ and $R^4$ each independently represent a hydrogen atom or a substituent, and $R^2$ represents a substituent.

The formula (II) will be explained.

$Z^1$ and $Z^2$ have the same meanings as that of $Z^1$ in formula (I), respectively, with the same preferable ranges. $Z^1$ and $Z^2$ may be the same or different from each other.

$L^1$, $L^2$ and $L^3$ have the same meanings as that of $L^1$ in formula (I), respectively, with the same preferable ranges. $L^1$, $L^2$ and $L^3$ may be the same or different from each other.

$Q^2$ represents a group bonded to the platinum through a carbon atom, an oxygen atom, a sulfur atom, a nitrogen atom or a phosphorous atom.

Examples of $Q^2$ bonded to the platinum through a carbon atom include an imino group, an aromatic hydrocarbon group (e.g., a phenyl group and a naphthyl group), an aromatic heterocyclic group (e.g., pyridine, pyrazine, pyrimidine, pyridazine, triazine, triazole, imidazole, pyrazole, thiophene and furan rings) and condensed rings containing these groups. These groups may be further substituted.

Examples of $Q^2$ bonded to the platinum through a nitrogen atom include a nitrogen-containing heterocyclic group (e.g., pyrrole, pyrazole, imidazole and triazole rings) and an amino group (e.g., an alkylamino group, an arylamino group, an acylamino group, an alkoxycarbonylamino group, an aryloxycarbonylamino group and a sulfonylamino group). These groups may be further substituted.

Examples of $Q^2$ bonded to the platinum through an oxygen atom include an oxy group, a carbonyloxy group, an alkoxy group, an aryloxy group, a heterocyclic oxy group, an acyloxy group and a silyloxy group.

Examples of $Q^2$ bonded to the platinum through a sulfur atom include a thio group, an alkylthio group, an arylthio group, a heterocyclic thio group and a carbonylthio group.

Examples of $Q^2$ bonded to the platinum through a phosphorous atom include a diarylphosphine group.

The group represented by $Q^2$ is preferably an aromatic hydrocarbon group bonded to the platinum through carbon, an aromatic heterocyclic group bonded to the platinum through carbon, a nitrogen-containing heterocyclic group bonded to the platinum through nitrogen, an aryloxy group or a carbonyloxy group; more preferably an aromatic hydrocarbon group bonded to the platinum through carbon, an aromatic heterocyclic group bonded to the platinum through carbon, an aryloxy group or a carbonyloxy group; and still more preferably an aromatic hydrocarbon group bonded to the platinum through carbon, an aromatic heterocyclic group bonded to the platinum through carbon, or a carbonyloxy group. $Q^2$ may have a substituent, if possible. As the substituent, those given as the examples of the substituent of the linking group $L^1$ in formula (I) can be applied.

$R^1$, $R^2$, $R^3$ and $R^4$ have the same meanings as those of $R^1$, $R^2$, $R^3$ and $R^4$ in formula (I), respectively, with the same preferable ranges.

The platinum complex represented by formula (II) is preferably a platinum complex represented by formula (III).

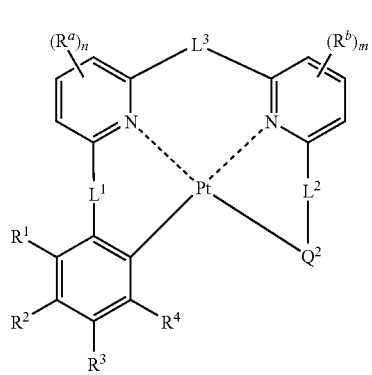

Formula (III)

In formula (III), $Q^2$ represents a group bonded to the platinum through a carbon atom, an oxygen atom, a sulfur atom, a nitrogen atom or a phosphorous atom. $L^1$, $L^2$ and $L^3$ each independently represent a single bond or a linking group. $R^1$, $R^3$ and $R^4$ each independently represent a hydrogen atom or a substituent, and $R^2$ represents a substituent. $R^a$ and $R^b$ each represent a substituent, and n and m each independently represent an integer of from 0 to 3.

The formula (III) will be explained.

$Q^2$, $L^1$, $L^2$, $L^3$, $R^1$, $R^2$, $R^3$ and $R^4$ have the same meanings as those of $Q^2$, $L^1$, $L^2$, $L^3$, $R^1$, $R^2$, $R^3$ and $R^4$ in formula (II), respectively, with the same preferable ranges.

$R^a$ and $R^b$ each represent a hydrogen atom or a substituent. As the substituent, those given as the examples of the substituent of $L^1$ can be applied. $R^a$ and $R^b$ are each independently preferably a hydrogen atom, an alkyl group, an aryl group, an amino group, an alkoxy group or a fluorine atom; more preferably an alkyl group or an aryl group; and still more preferably an alkyl group.

n and m each represent an integer of from 0 to 3.

The platinum complex represented by formula (III) is preferably a platinum complex represented by formula (IV).

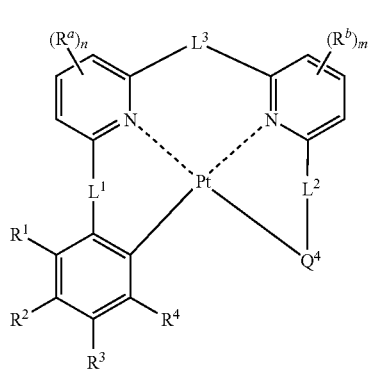

Formula (IV)

In formula (IV), $Q^4$ represents an aromatic hydrocarbon group or an aromatic heterocyclic group, each bonded to the platinum through a carbon atom or a nitrogen atom. $L^1$, $L^2$ and $L^3$ each independently represent a single bond or a linking group. $R^1$, $R^3$ and $R^4$ each independently represent a hydrogen atom or a substituent, and $R^2$ represents a substituent $R^a$ and $R^b$ each represent a substituent, and n and m each independently represent an integer of from 0 to 3.

The formula (IV) will be explained.

$L^1$, $L^2$, $L^3$, $R^1$, $R^2$, $R^3$, $R^4$, $R^a$, $R^b$, n and m have the same meanings as those of $L^1$, $L^2$, $L^3$, $R^1$, $R^2$, $R^3$, $R^4$, $R^a$, $R^b$, n and m in formula (III), respectively, with the same preferable ranges.

$Q^4$ represents an aromatic hydrocarbon group or an aromatic heterocyclic group, each bonded to the platinum through a carbon atom or a nitrogen atom. Examples of $Q^4$ bonded to the platinum through a carbon atom include a benzene ring, a pyridine ring, a pyrimidine ring, a pyridazine ring, a pyrazine ring, a triazole ring, a pyrazole ring, an imidazole ring, a thiophene ring, a furan ring, and benzo-condensed or pyrido-condensed rings of these compounds. Examples of $Q^4$ bonded to the platinum through a nitrogen atom include a pyrrole ring, an imidazole ring, a pyrazole ring, a triazole ring, and benzo-condensed or pyrido-condensed rings of these compounds. $Q^4$ may have a substituent, if possible. As the substituent, those given as the examples of the substituent of the linking group $L^1$ in formula (I) can be applied.

Among the platinum complexes represented by formula (IV), a platinum complex represented by formula (V) is a preferable embodiment.

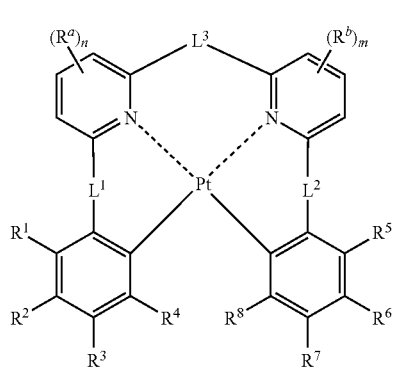

Formula (V)

In formula (V), $L^1$, $L^2$ and $L^3$ each independently represent a single bond or a linking group. $R^1$, $R^3$, $R^4$, $R^5$, $R^7$ and $R^8$ each independently represent a hydrogen atom or a substituent, and $R^2$ and $R^6$ each independently represent a substituent. $R^a$ and $R^b$ each independently represent a substituent, and n and m each independently represent an integer of from 0 to 3.

The formula (V) will be explained.

$L^1$, $L^2$, $L^3$, $R^1$, $R^2$, $R^3$, $R^4$, $R^a$, $R^b$, n and m have the same meanings as those of $L^1$, $L^2$, $L^3$, $R^1$, $R^2$, $R^3$, $R^4$, $R^a$, $R^b$, n and m in formula (IV), respectively, with the same preferable ranges. $R^5$, $R^6$, $R^7$ and $R^8$ have the same meanings as those of $R^1$, $R^2$, $R^3$ and $R^4$, respectively, with the same preferable ranges. $R^5$, $R^6$, $R^7$ and $R^8$ may be the same or different from each other.

The following illustrates specific examples of the compound containing a partial structure represented by formula (I) and the compound represented by any one of formulae (II) to (V). In the present invention, however, the compounds are not limited to these. In the following exemplified compound Nos. 62 and 225, "D" represents a deuterium atom.

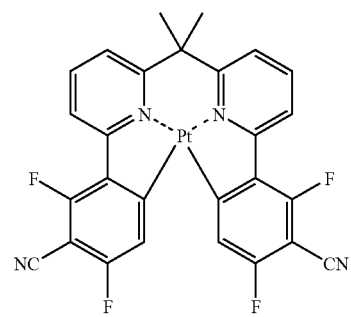

1

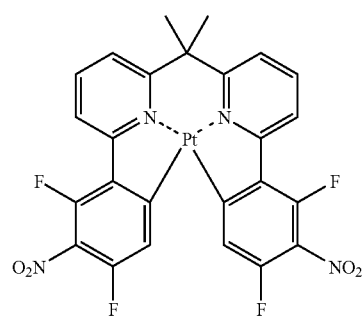

2

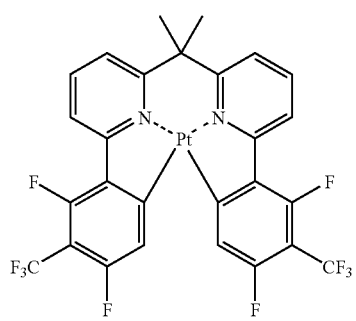

3

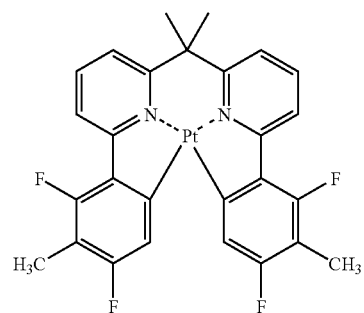

4

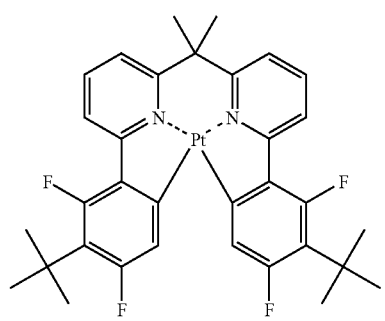

5

6
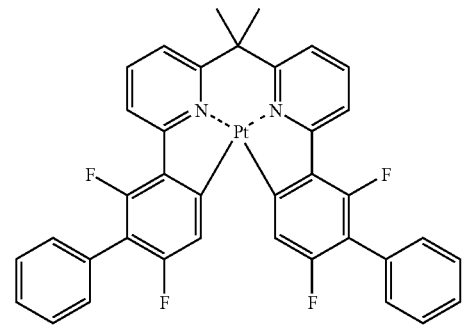
7
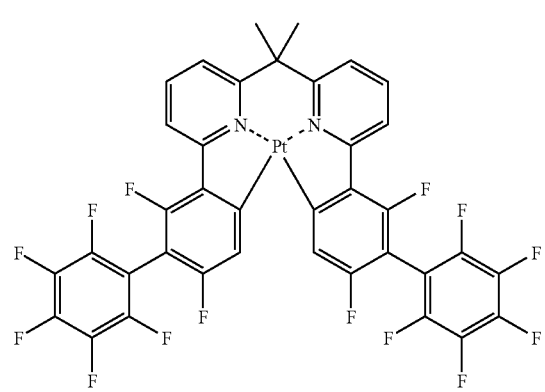
8
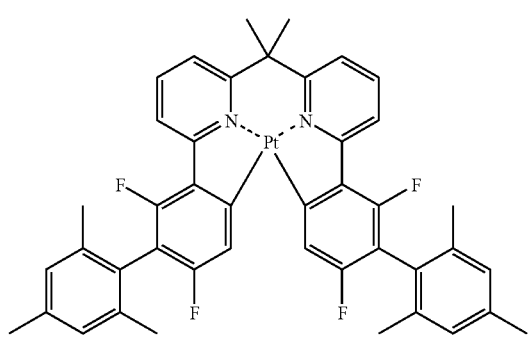
9
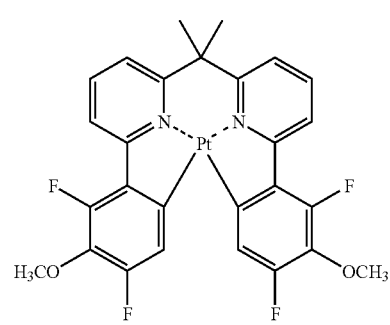
10
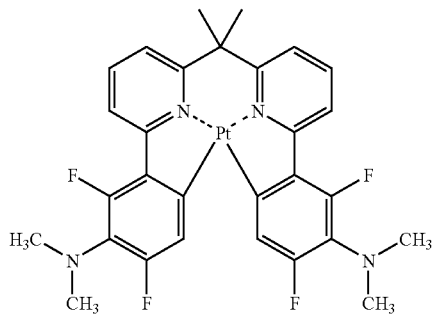
11
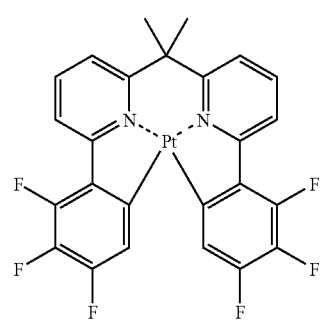
12
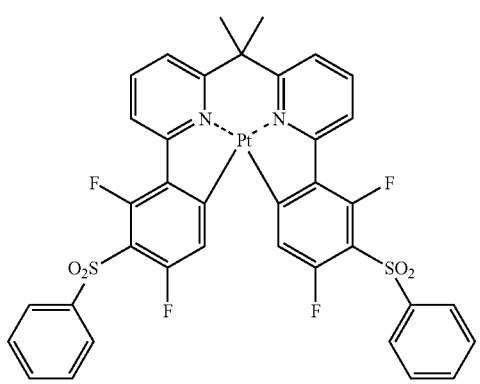
13
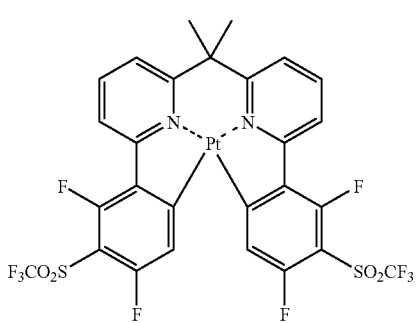
14
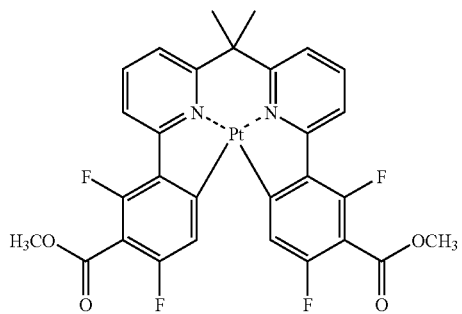

-continued
15
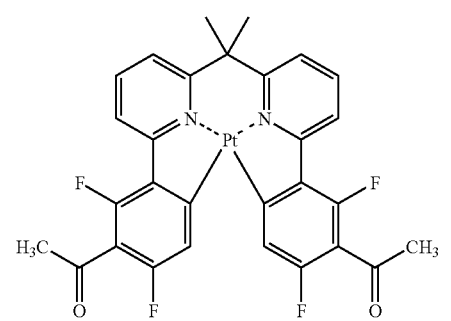
16
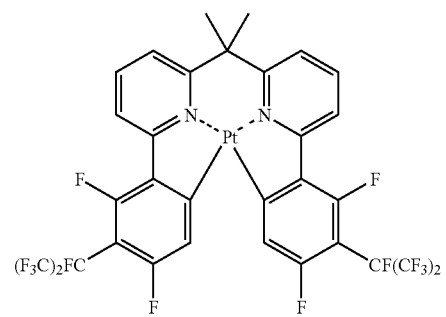
17
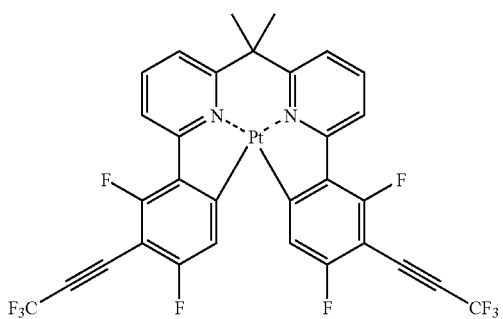
18
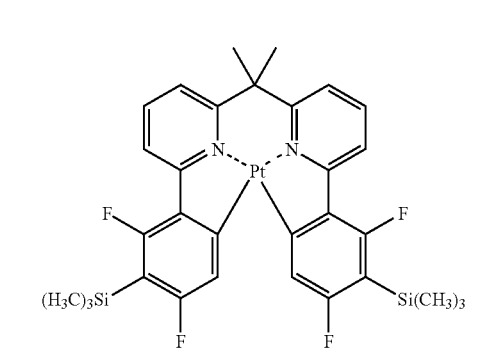
19
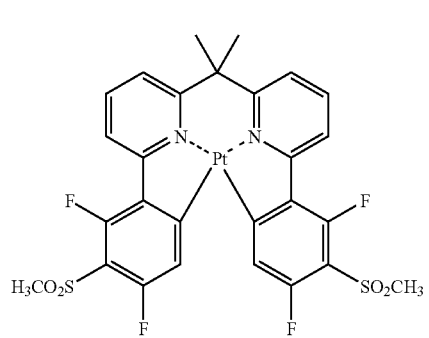
-continued
20
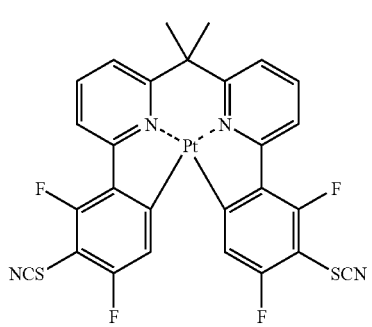
21
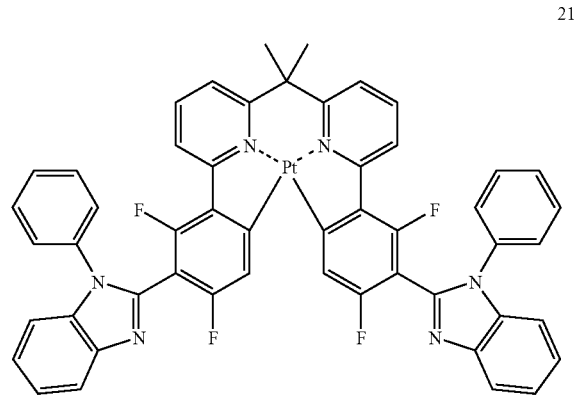
22
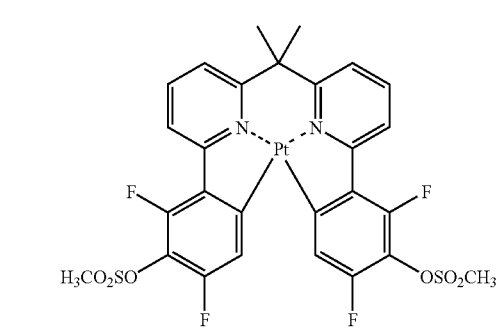
23
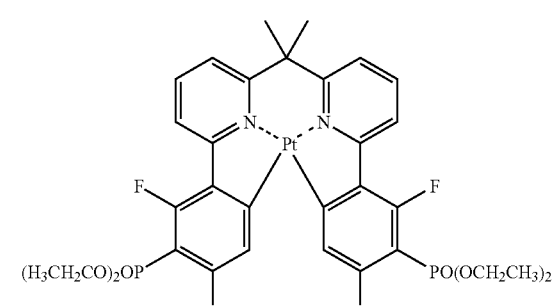
24
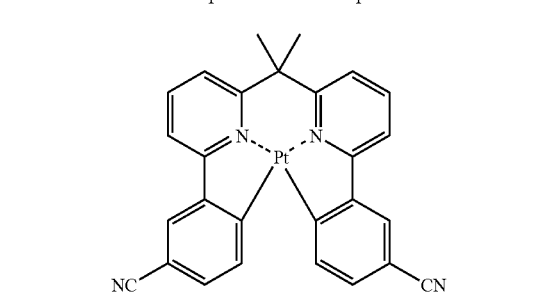

-continued
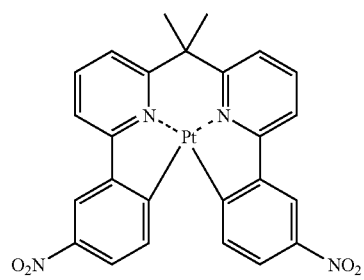
25
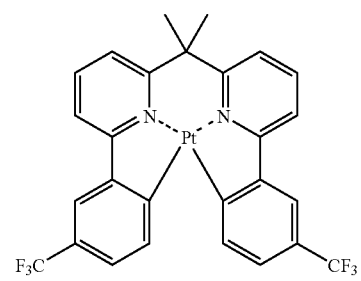
26
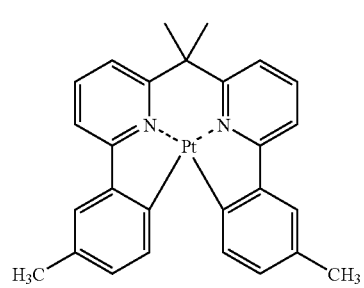
27
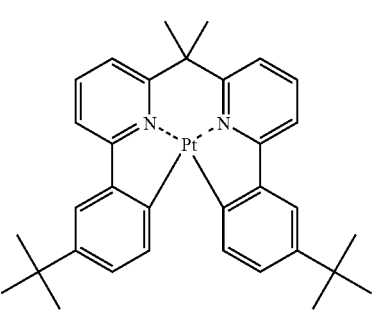
28
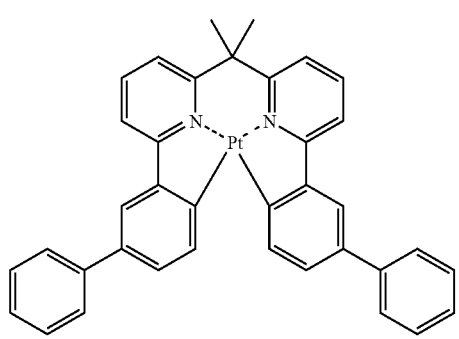
29
-continued
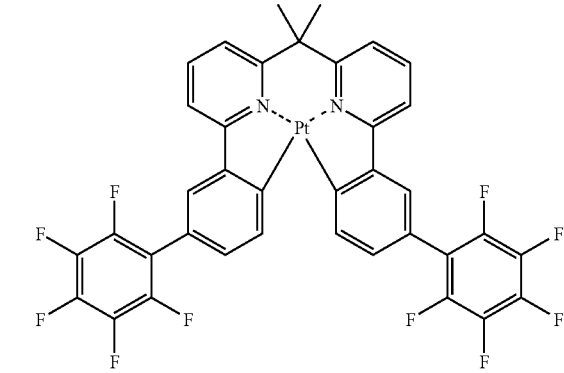
30
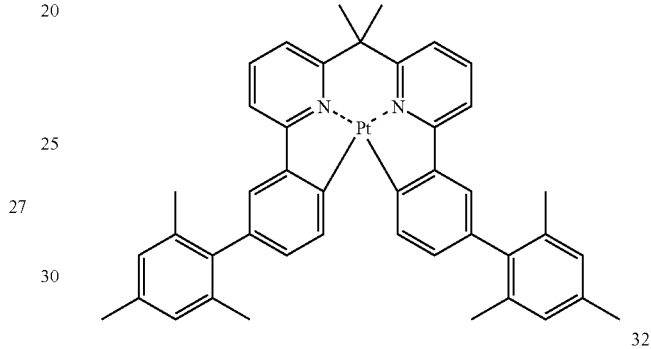
31
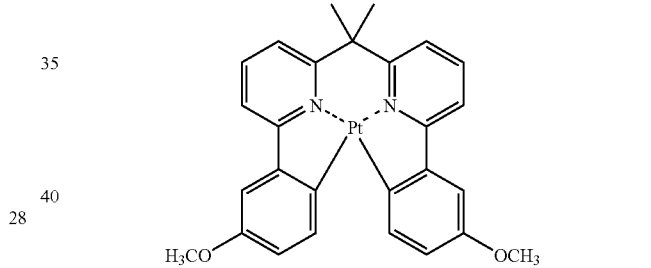
32
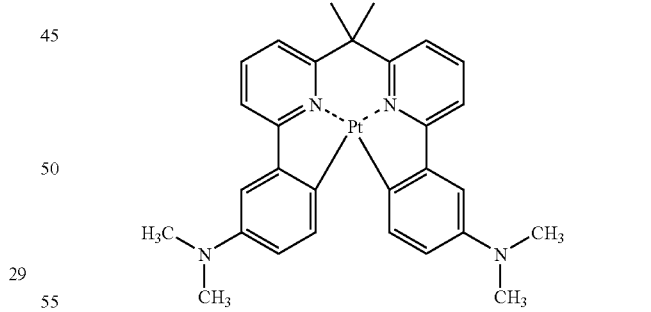
33
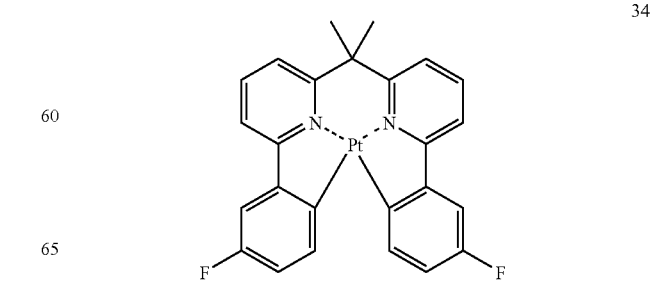
34

35
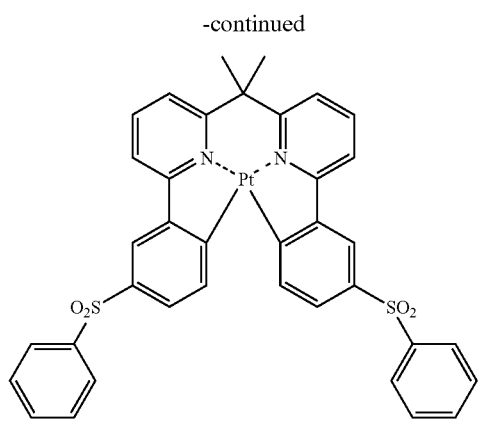
36
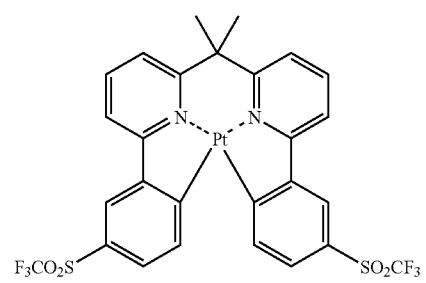
37
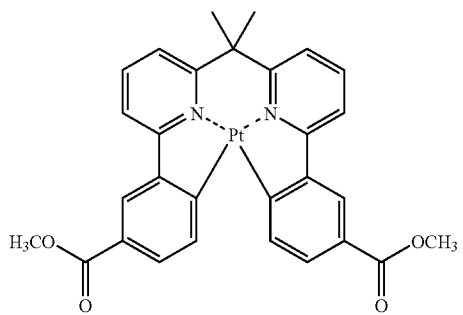
38
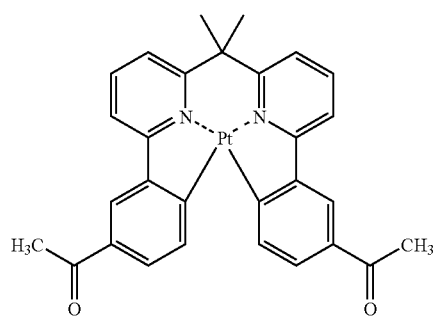
39
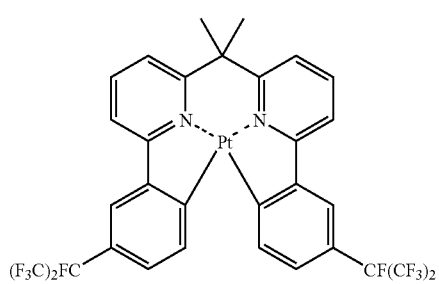
40
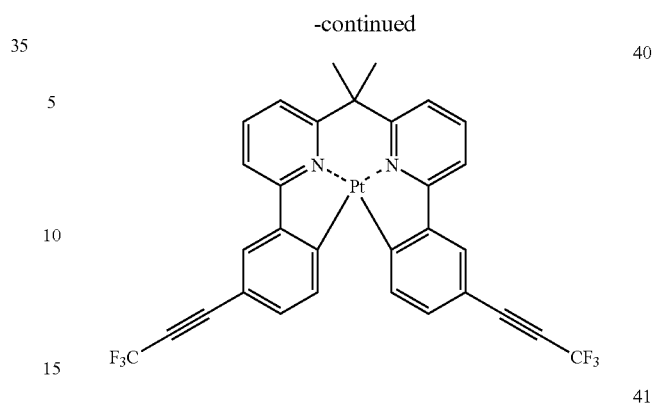
41
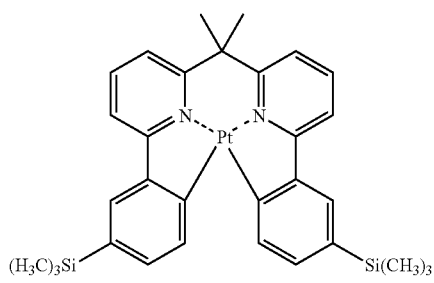
42
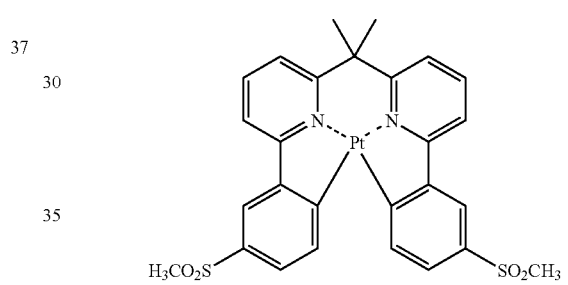
43
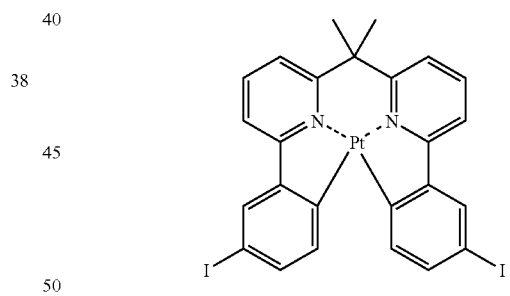
44
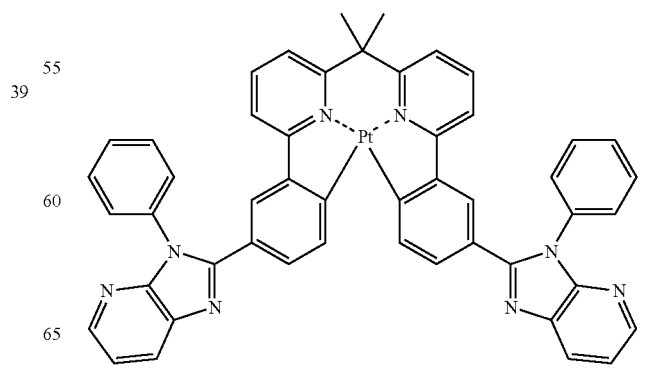

-continued
45
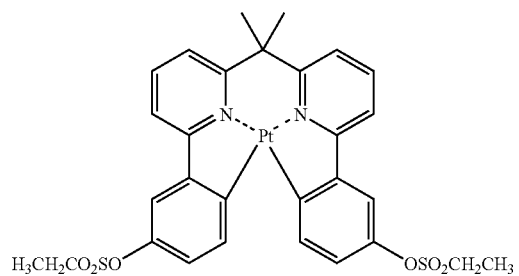
46
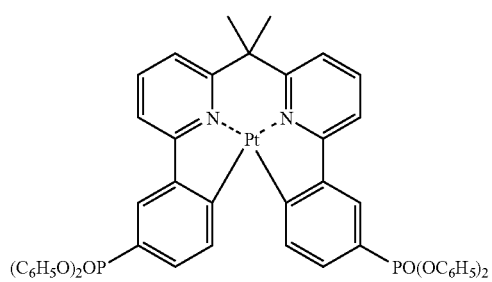
47
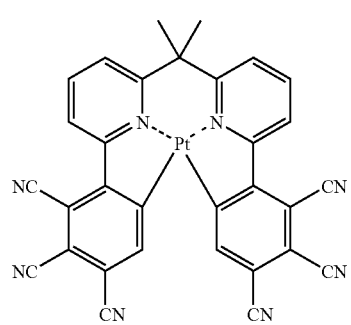
48
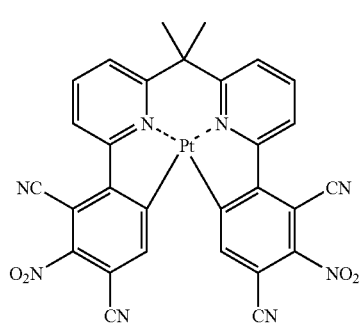
49
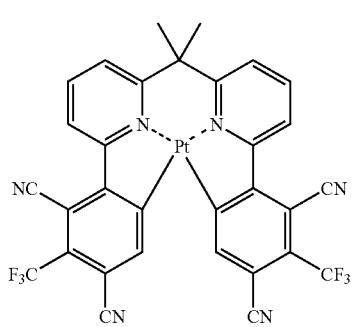
-continued
50
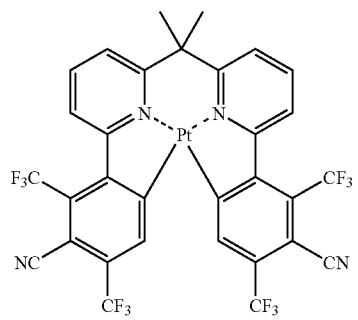
51
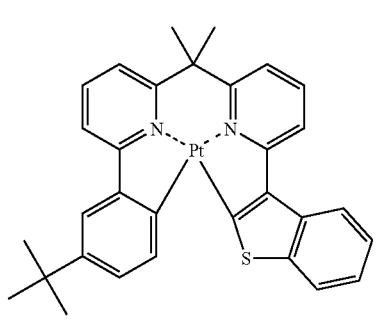
52
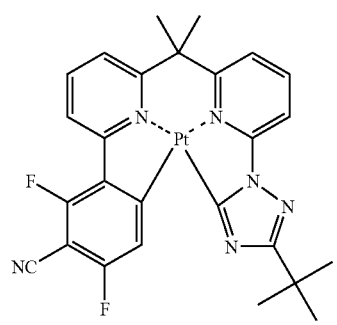
53
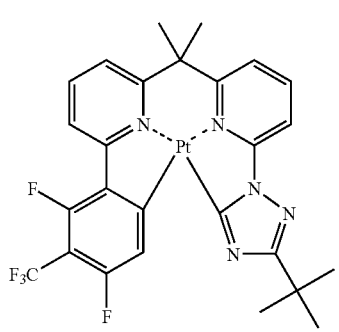
54

-continued
55
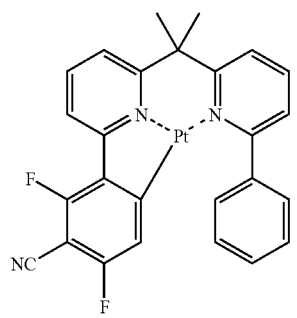
56
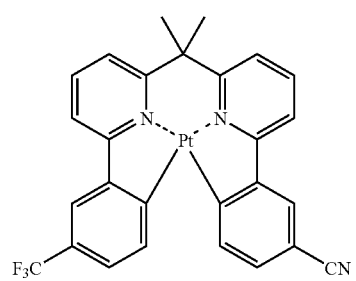
57
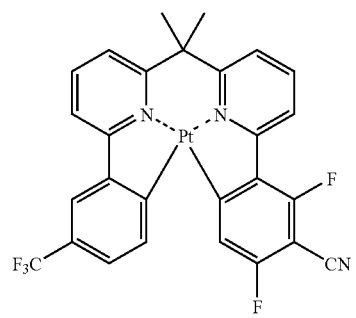
58
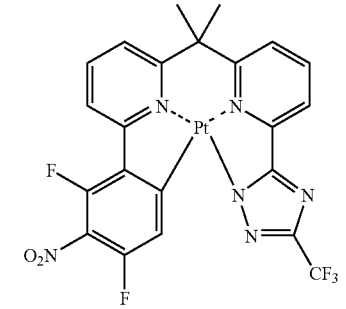
59
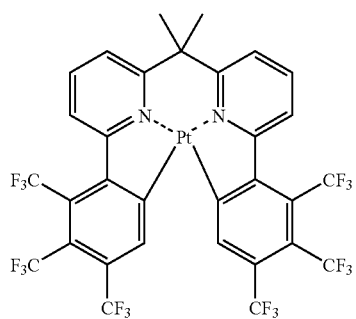
-continued
60
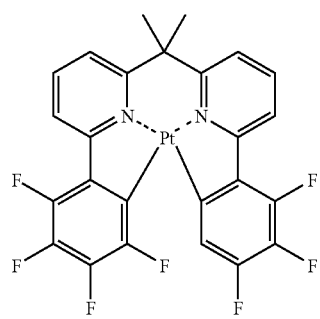
61
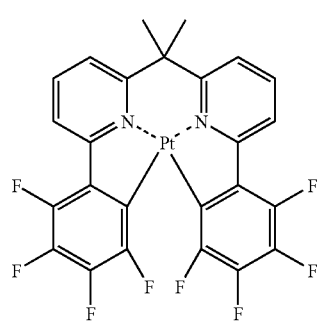
62
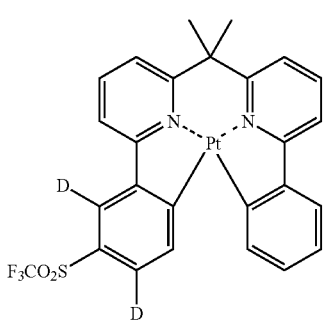
63
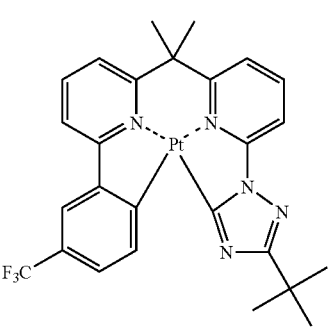
64
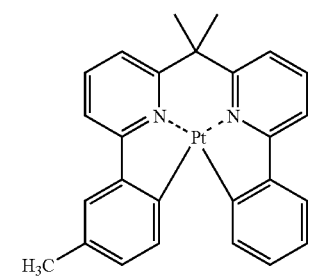

65 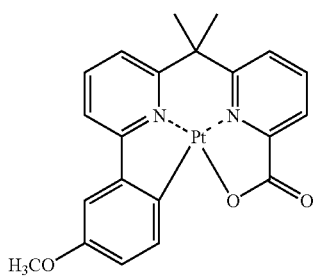
66 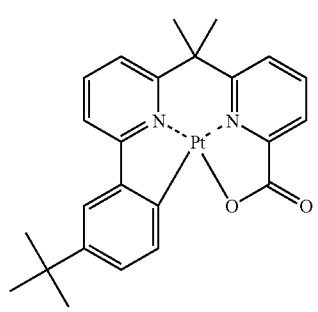
67 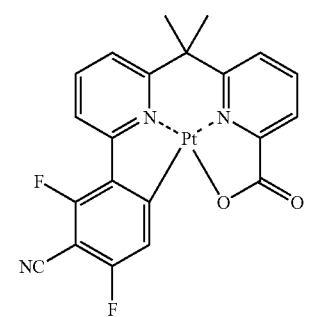
68 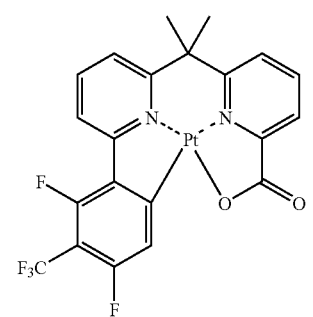
69 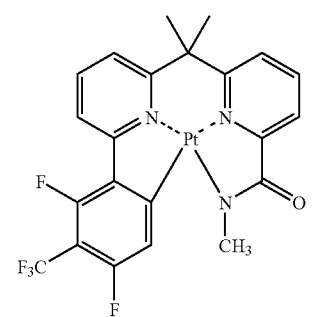
70 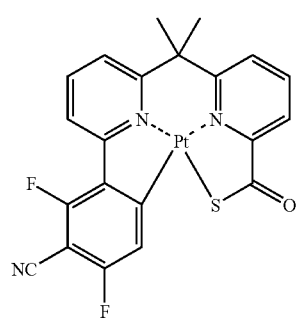
71 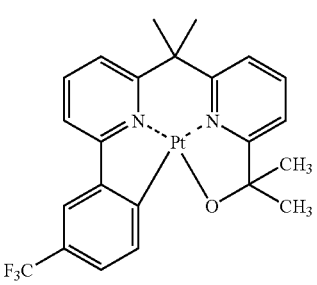
72 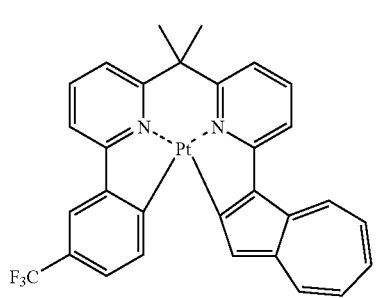
73 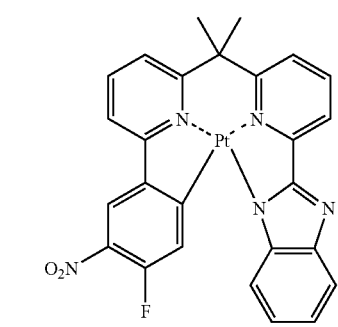
74 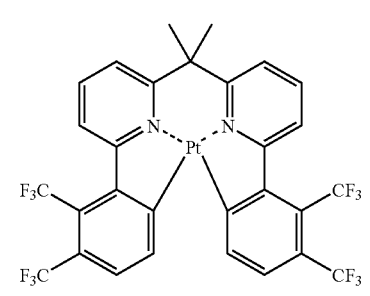

75
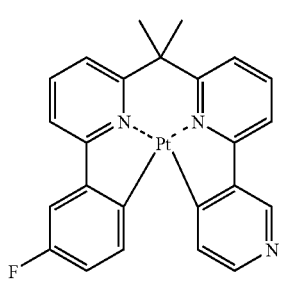
76
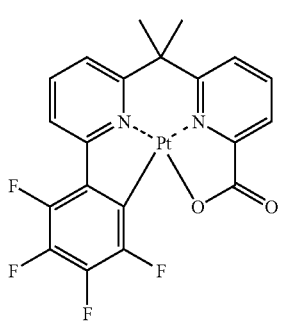
77
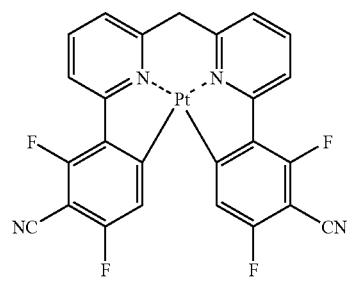
78
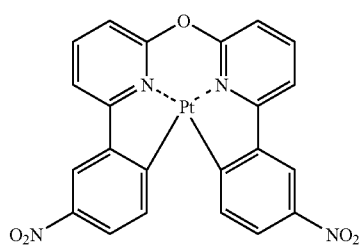
79
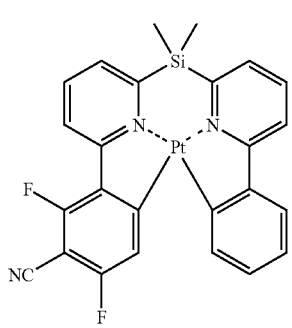
80
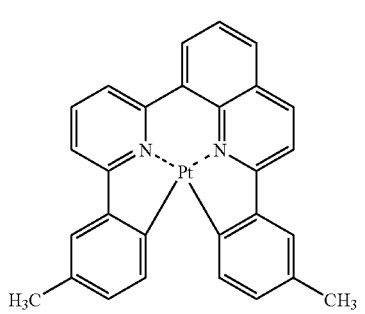
81
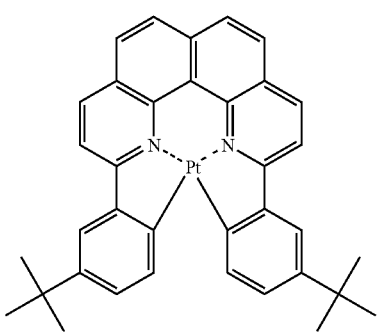
82
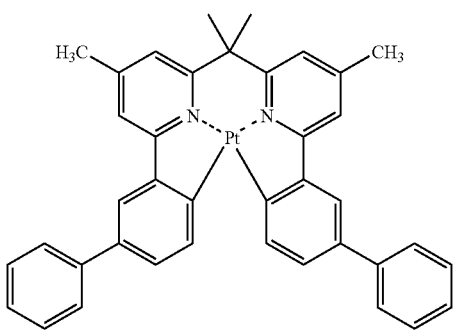
83
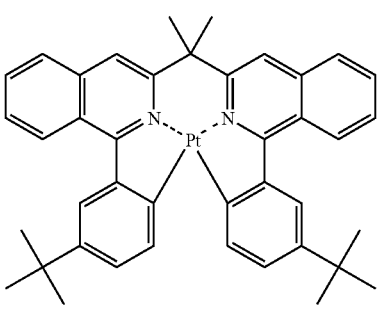
84
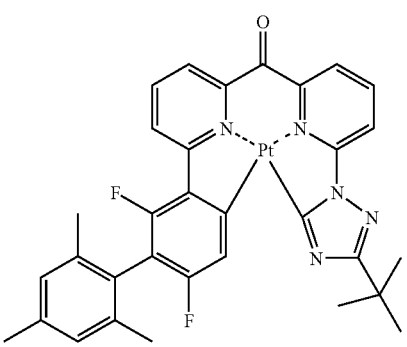

85
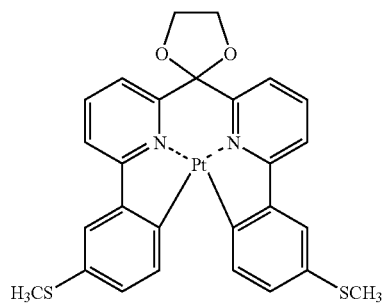
86
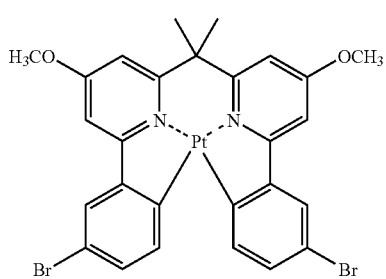
87
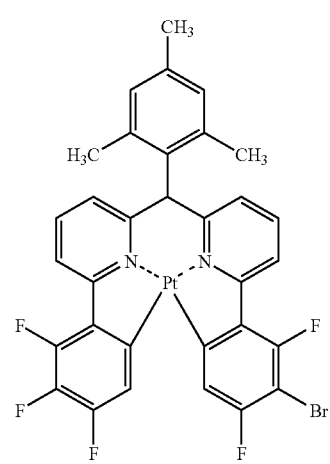
88
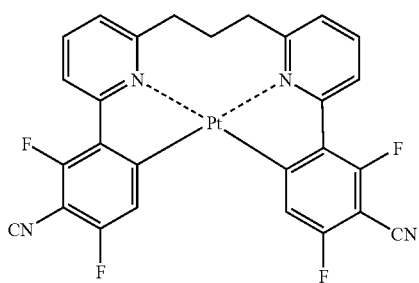
89
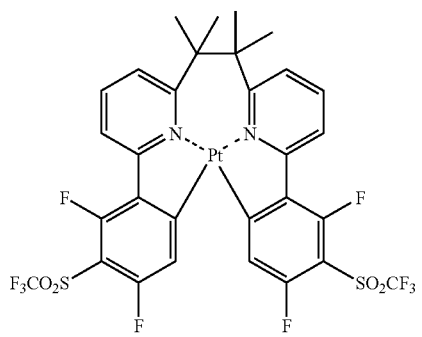
90
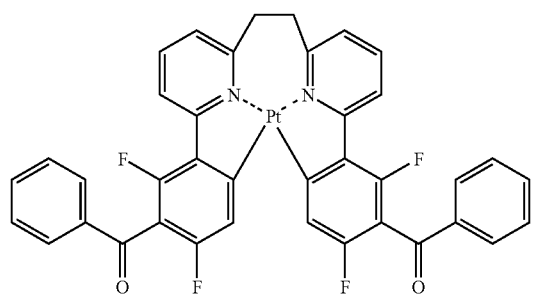
91
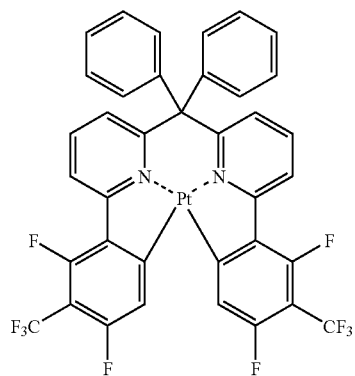
92

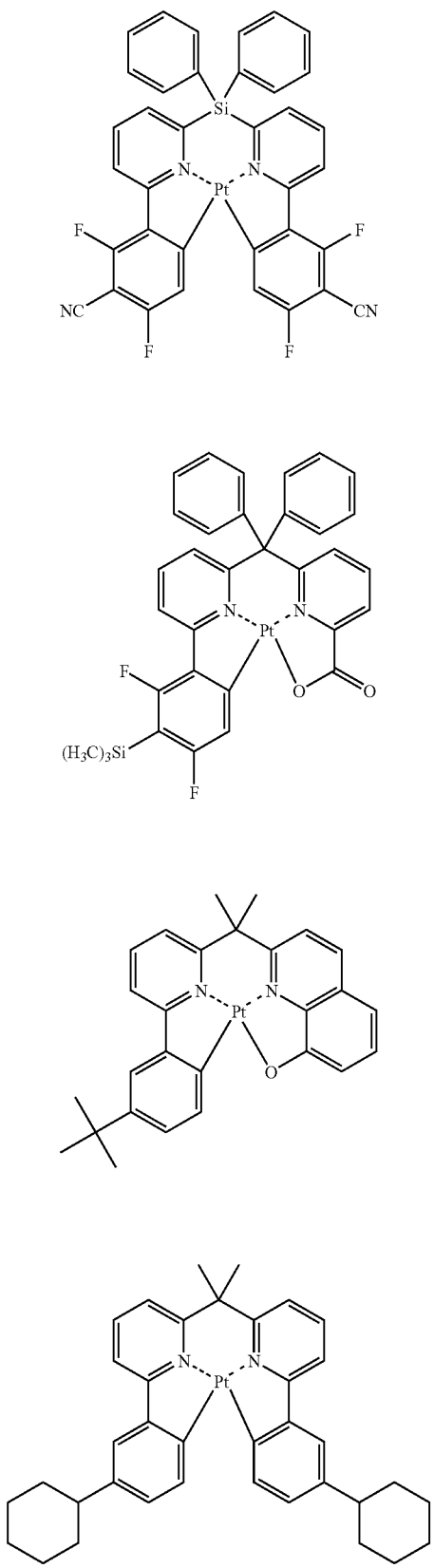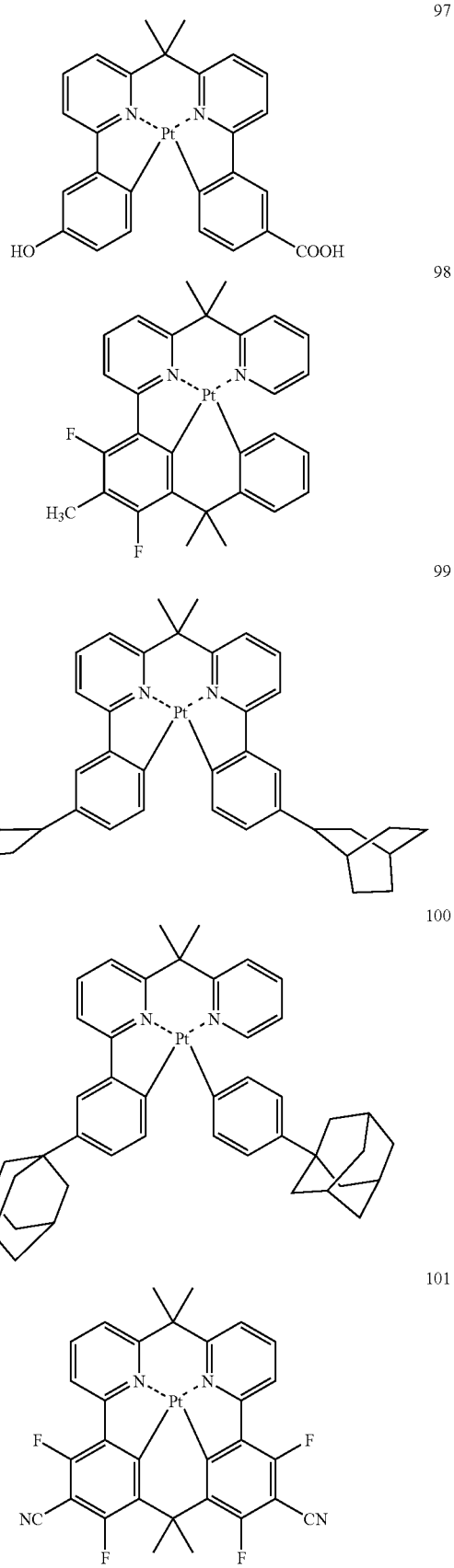

102
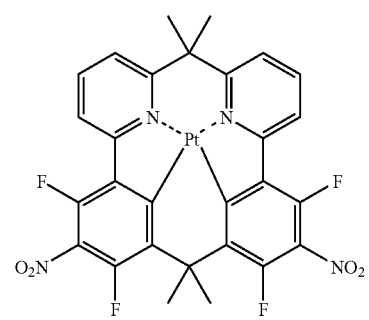
103
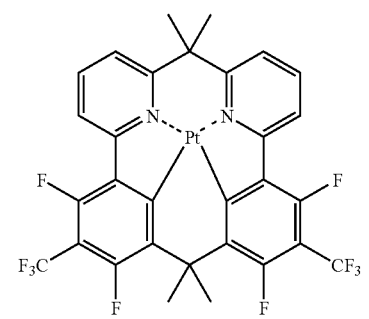
104
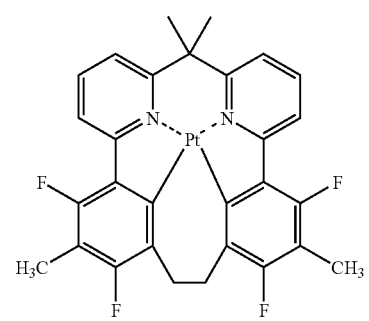
105
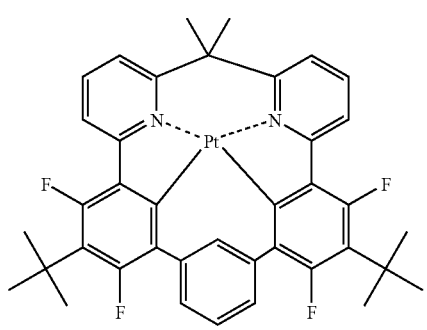
106
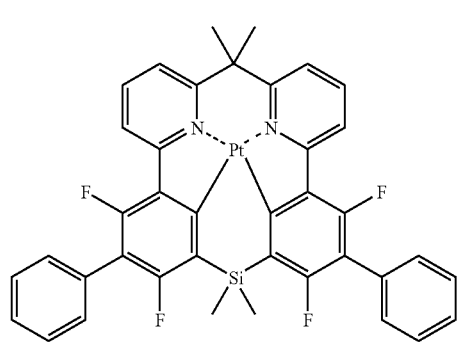
107
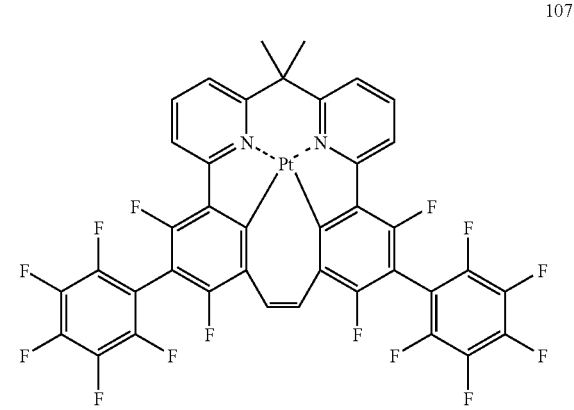
108
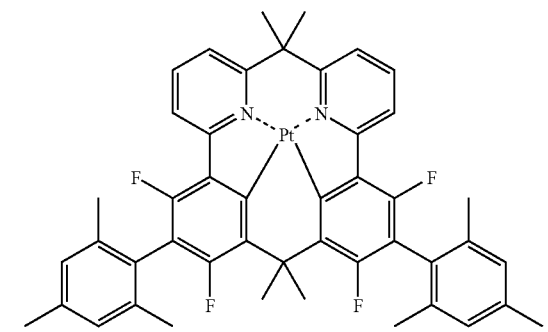
109
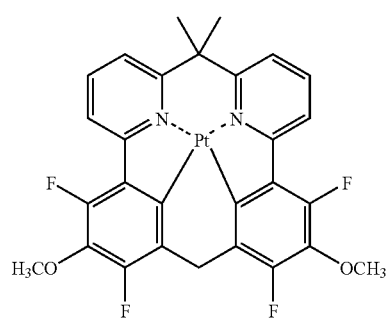
110
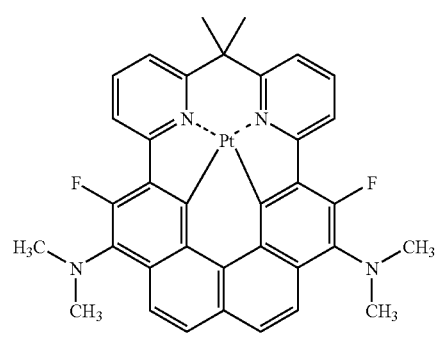

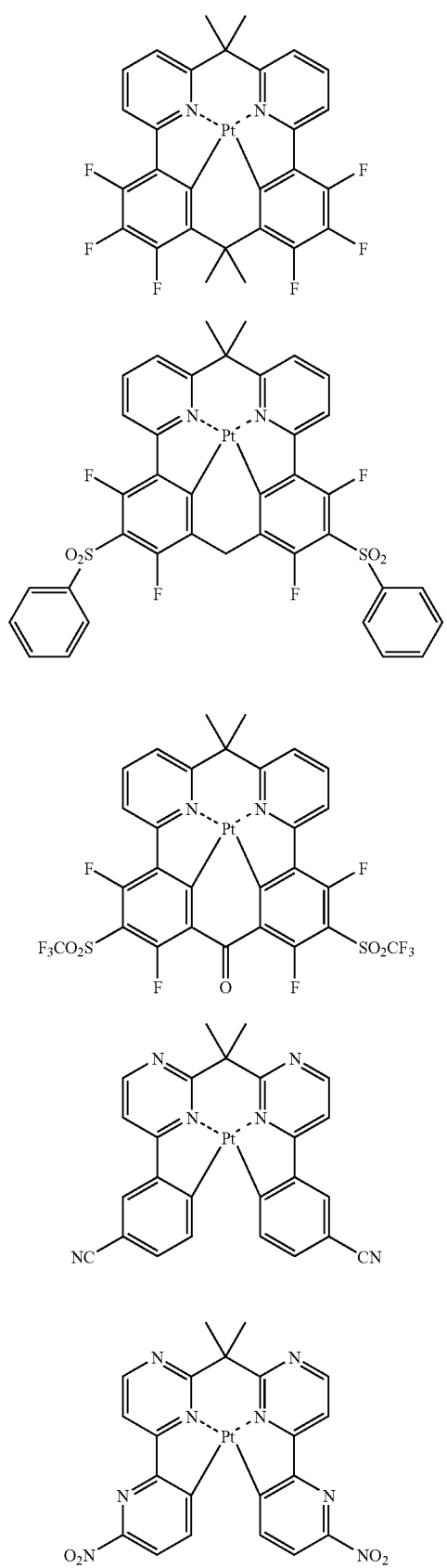
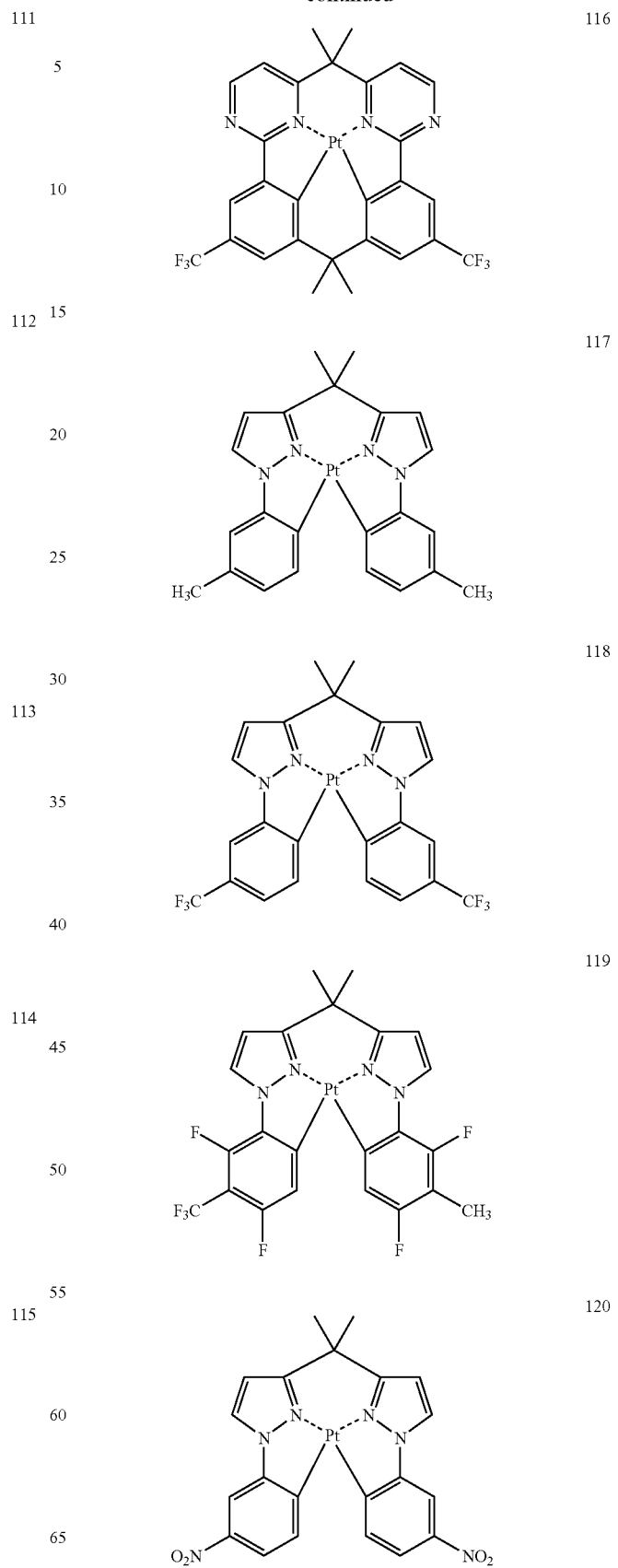

-continued
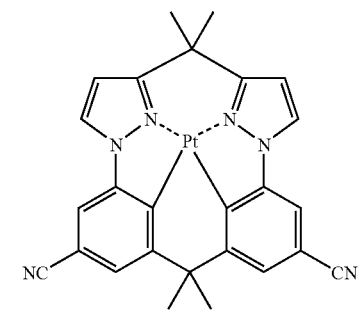
121
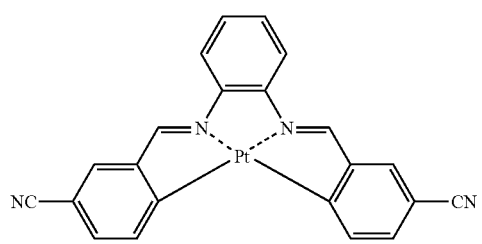
122
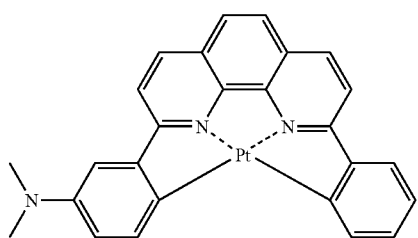
123
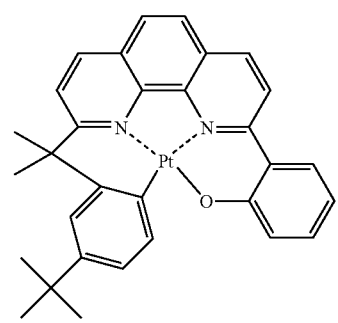
124
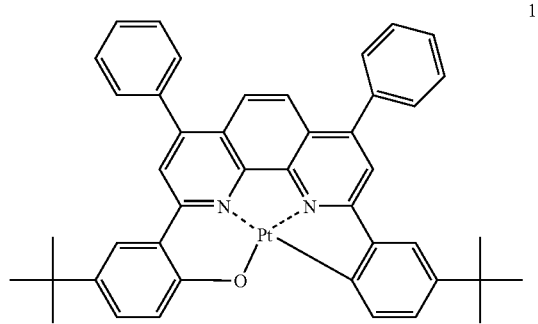
125
-continued
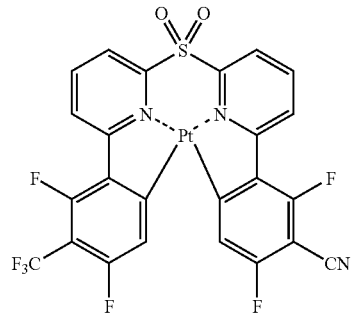
126
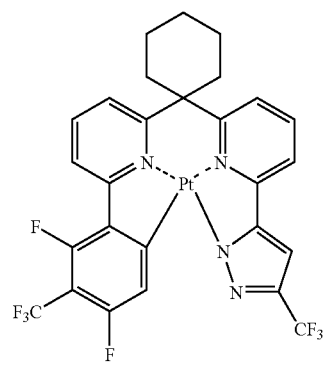
127
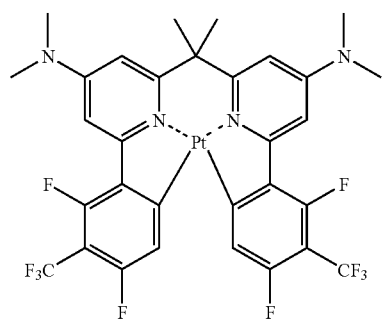
128
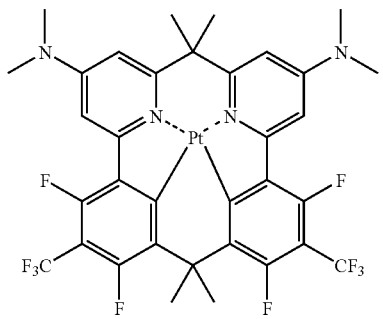
129

-continued
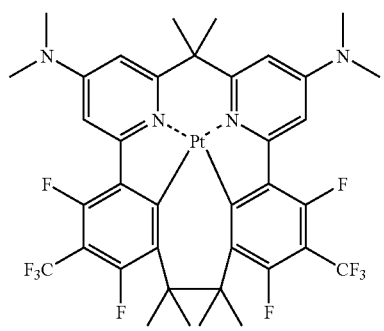
130
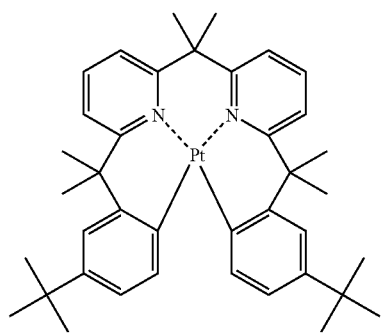
131
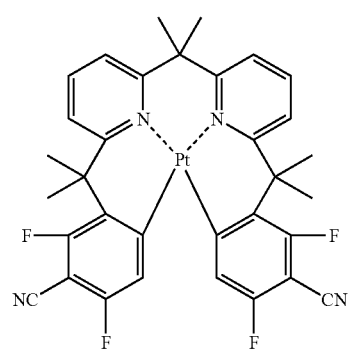
132
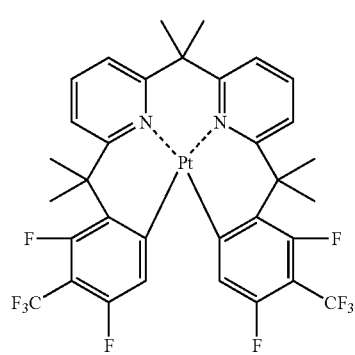
133
-continued
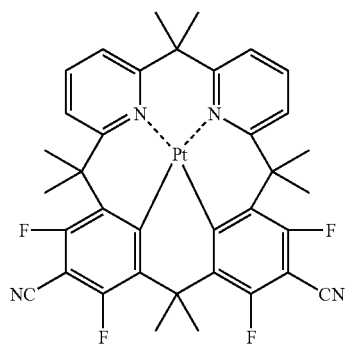
134
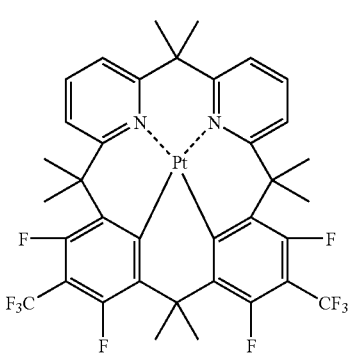
135
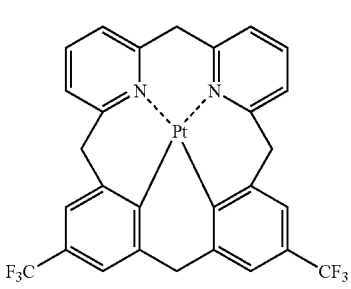
136
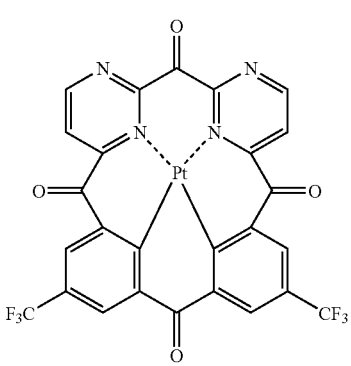
137

138 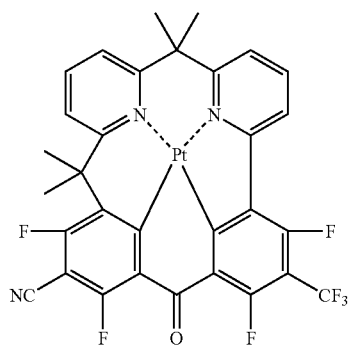
139 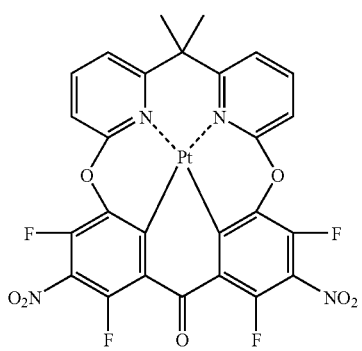
140 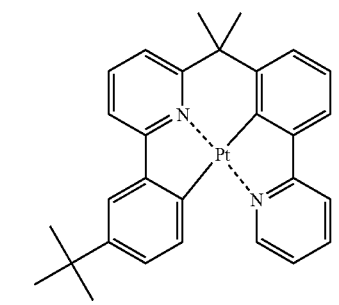
141
142
143 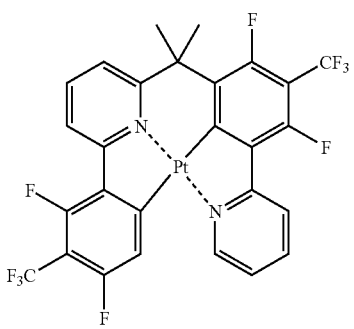
144 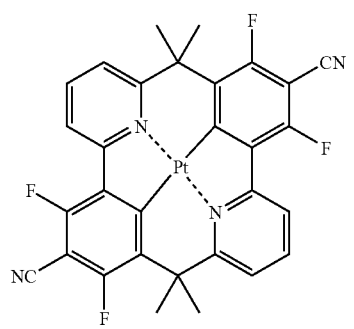
145 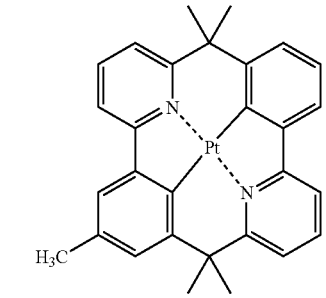
146 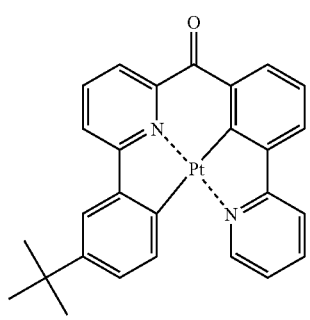
147 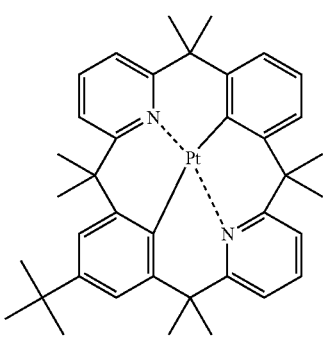

-continued
148
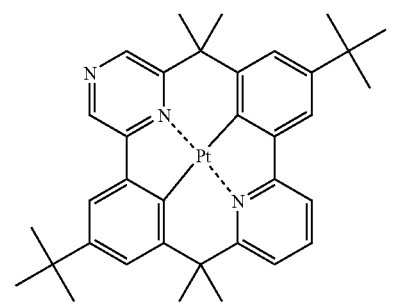
149
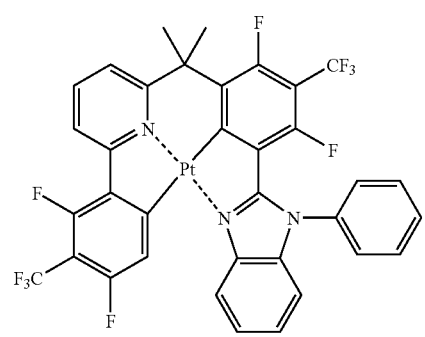
150
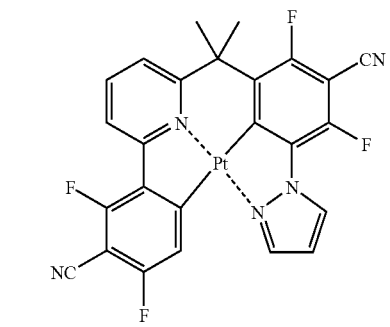
151
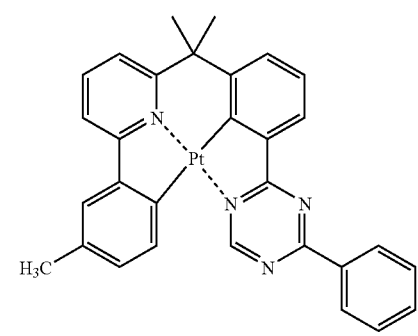
152
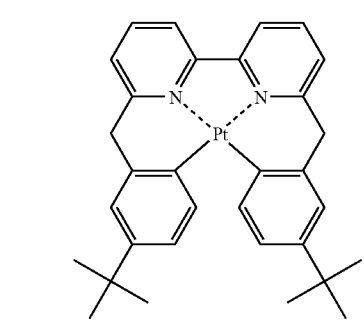
-continued
153
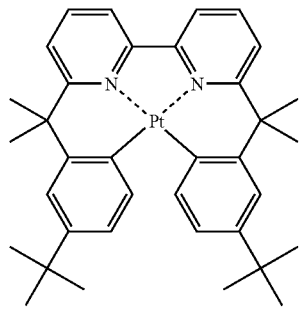
154
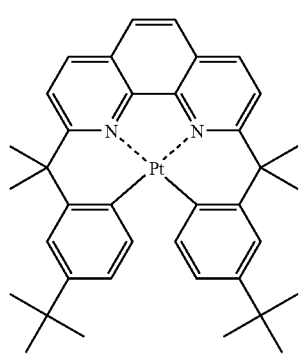
155
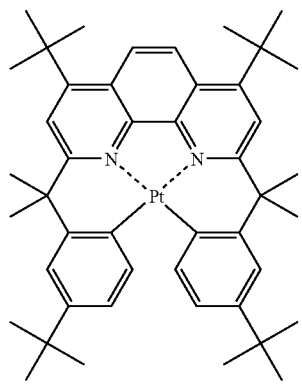
156
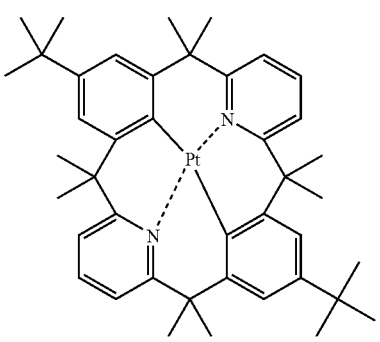

-continued
157
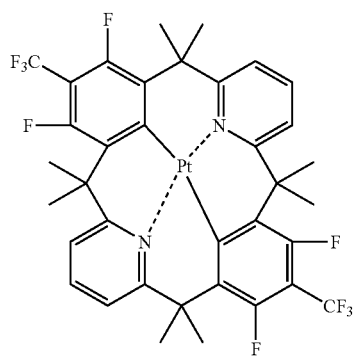
158
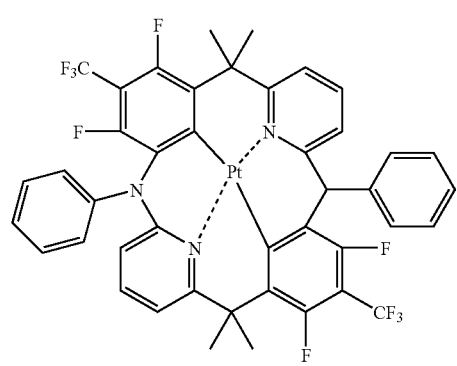
159
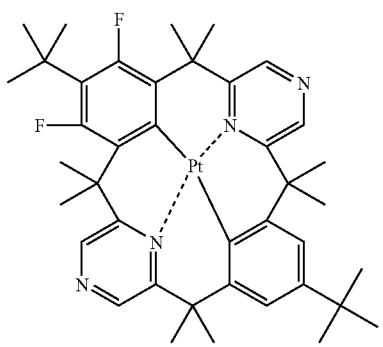
160
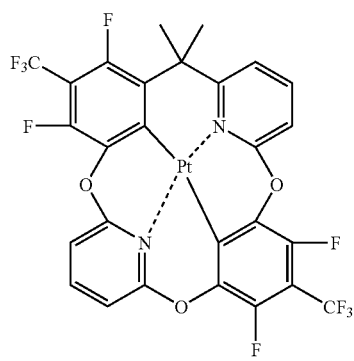
-continued
161
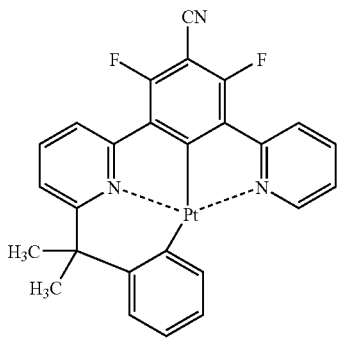
162
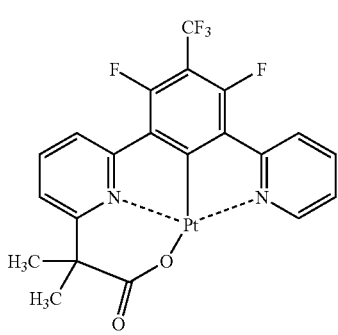
163
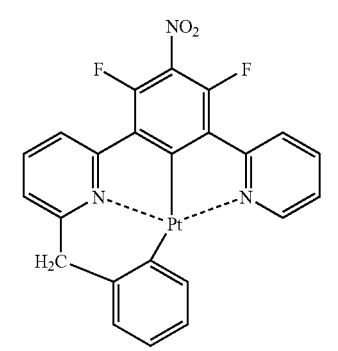
164
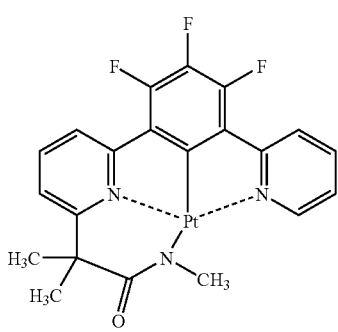

-continued
165
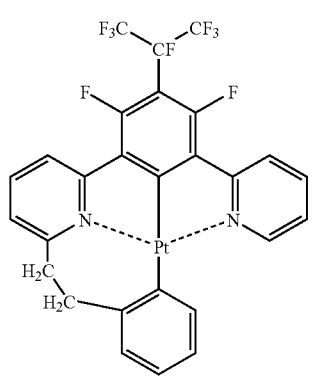
166
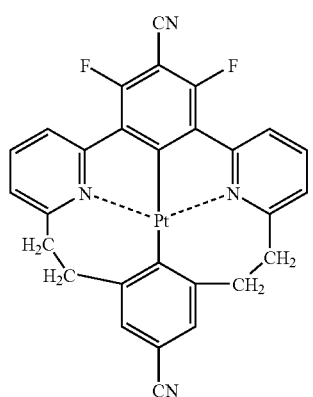
167
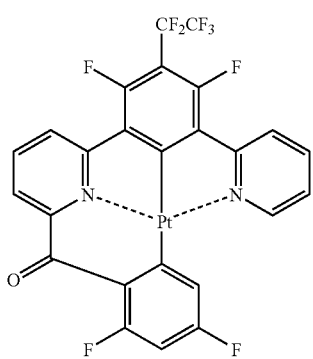
168
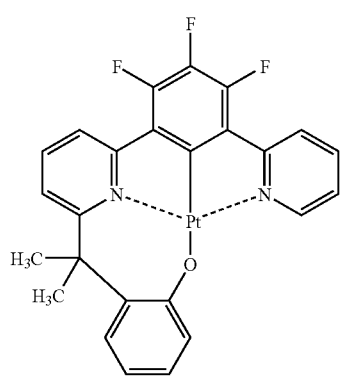
-continued
169
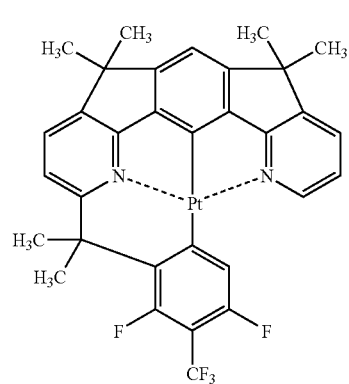
170
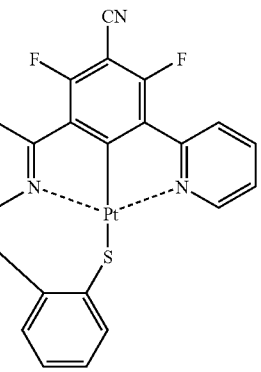
171
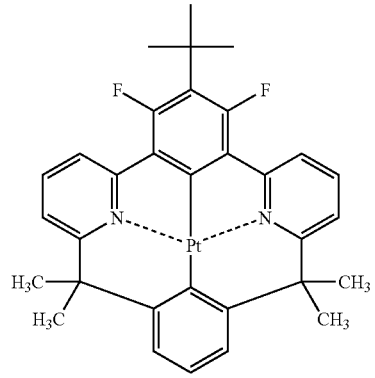
172
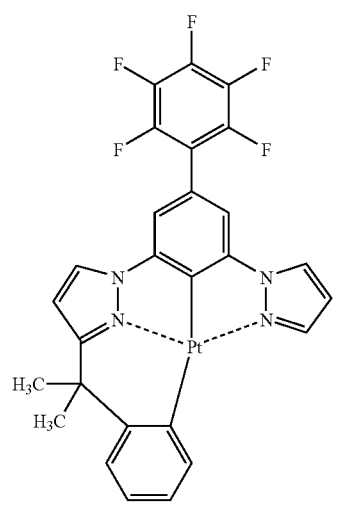

-continued
173
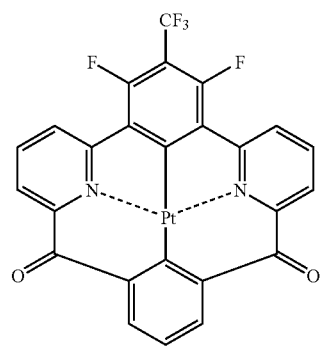
174
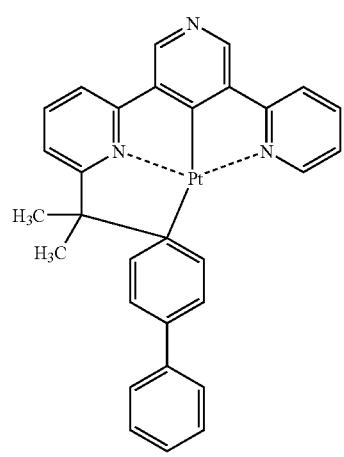
175
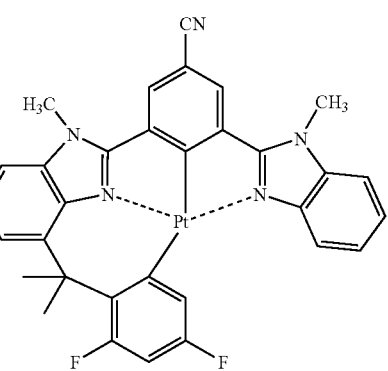
176
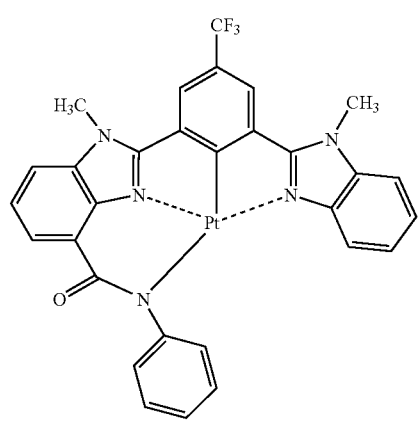
-continued
177
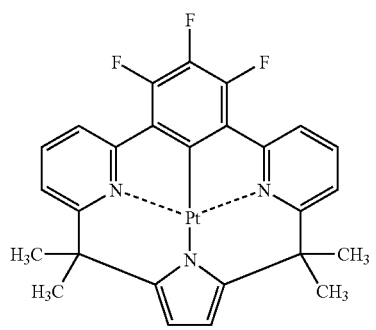
178
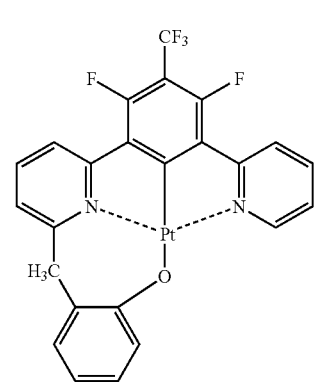
179
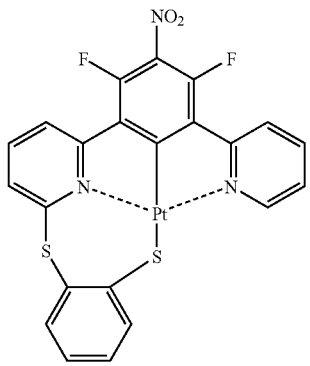
180
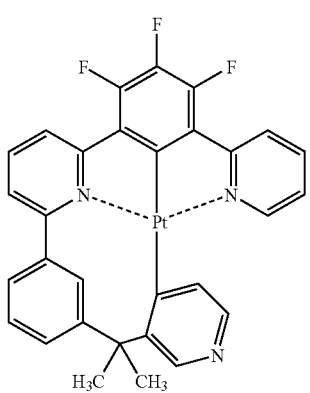

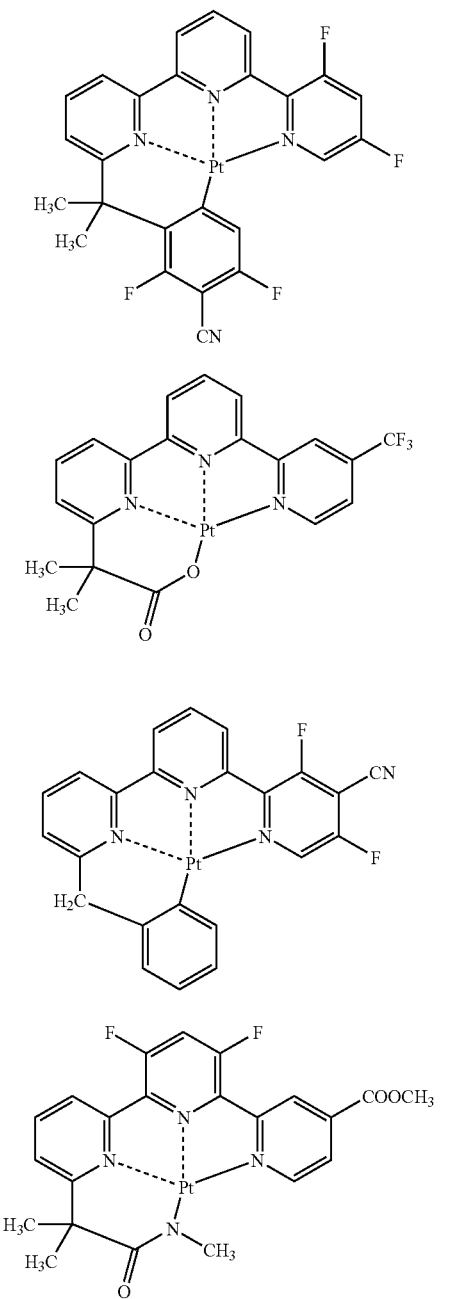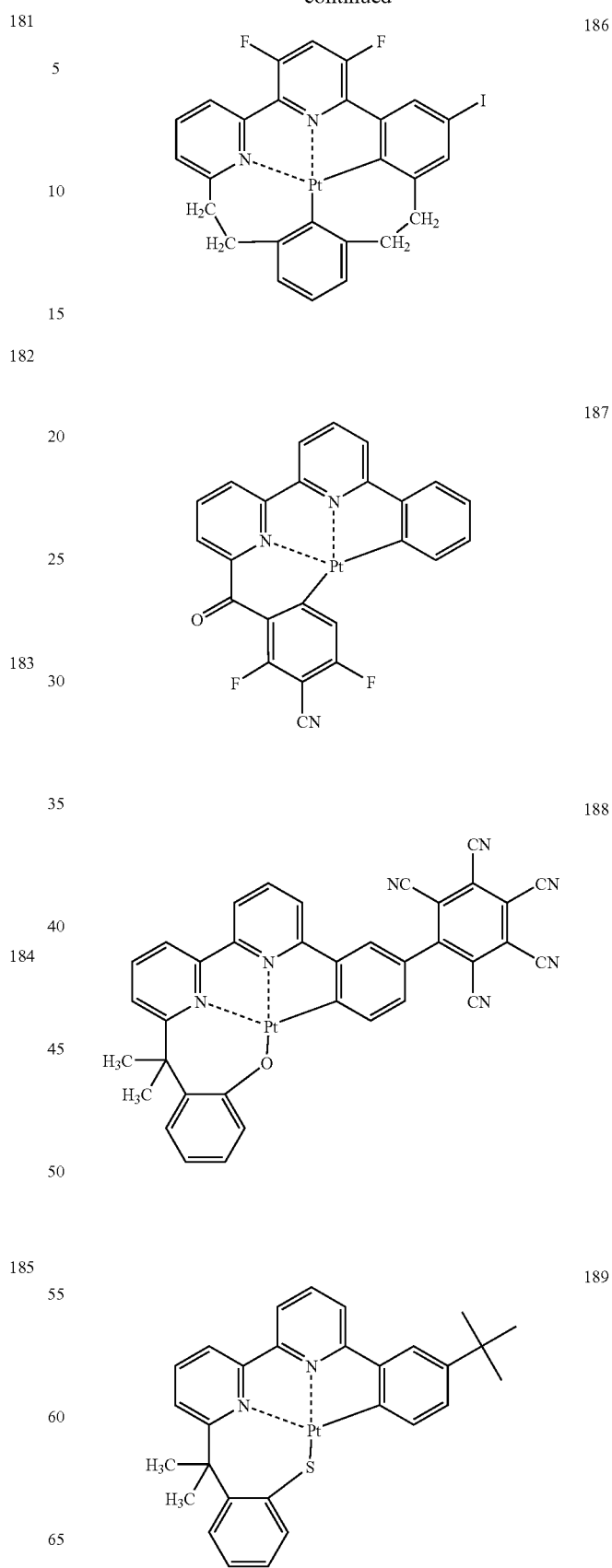

190
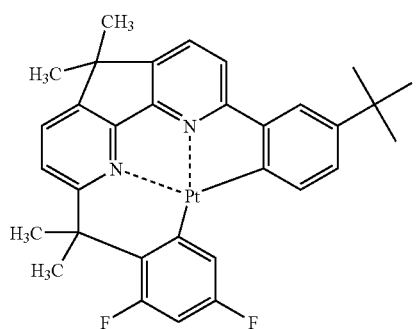
191
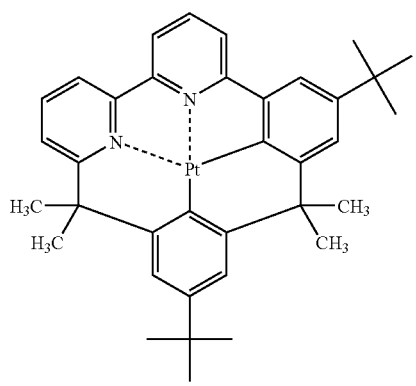
192
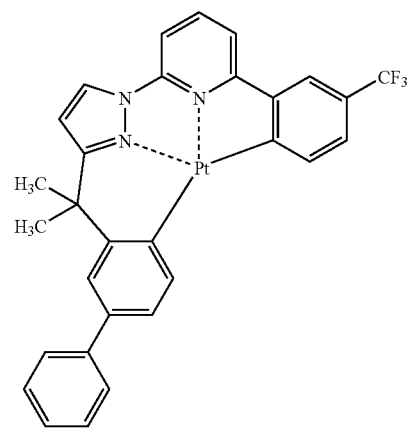
193
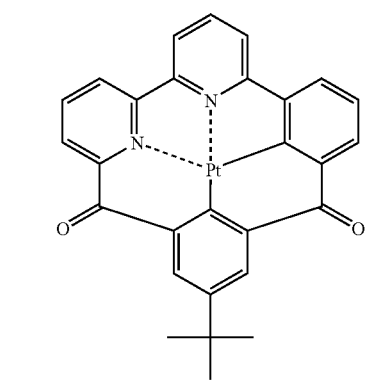
194
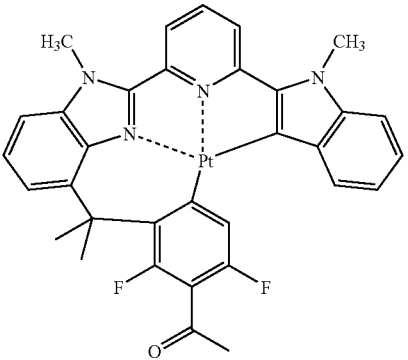
195
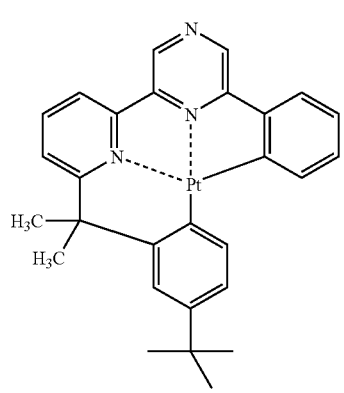
196
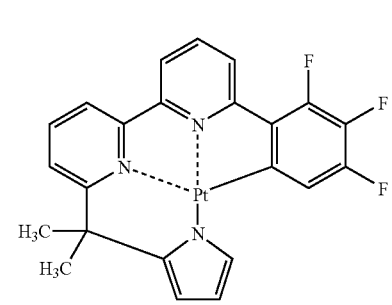
197
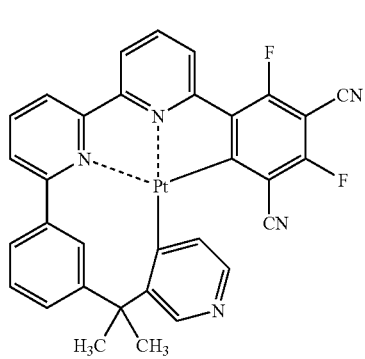

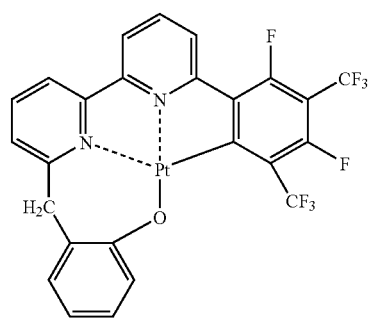
198
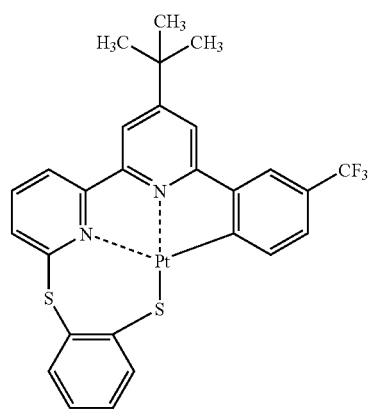
199
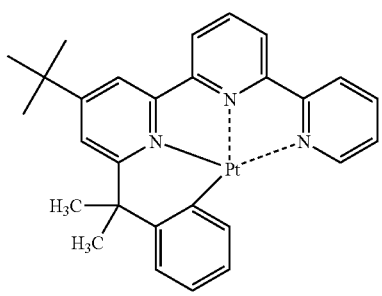
200
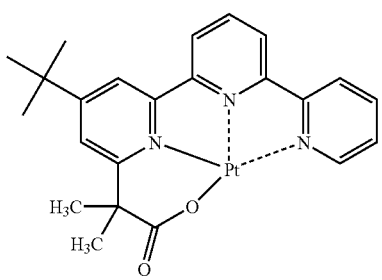
201
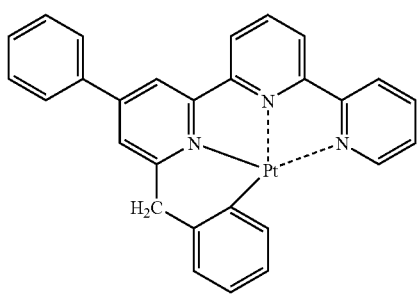
202
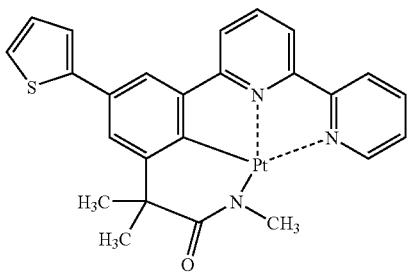
203
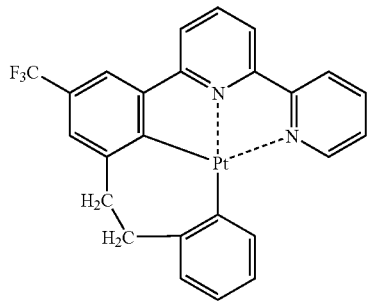
204
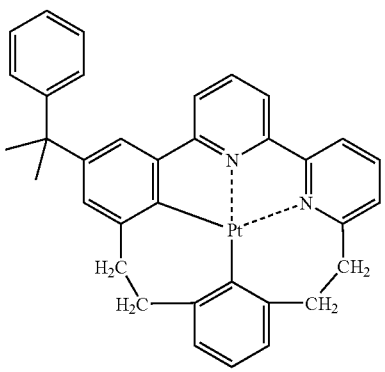
205
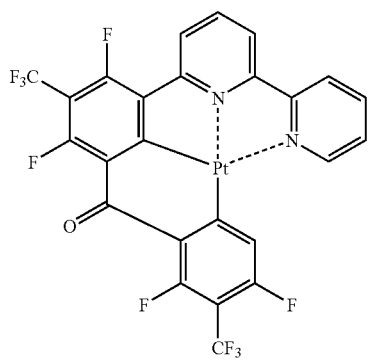
206
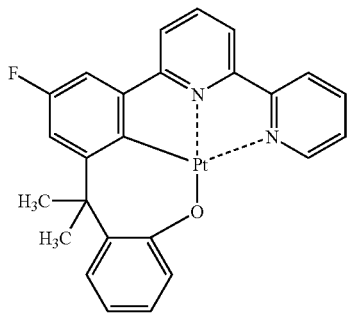
207

-continued
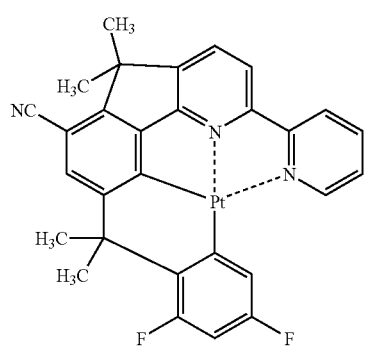
208
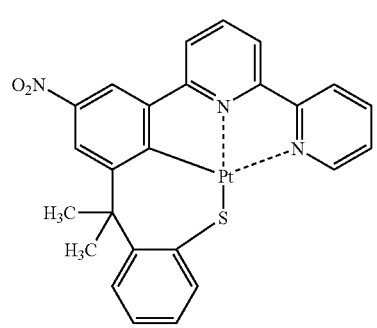
209
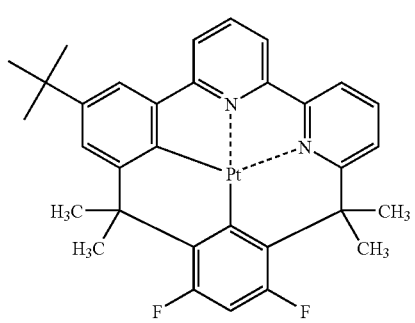
210
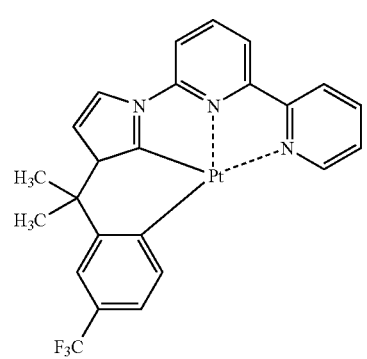
211
-continued
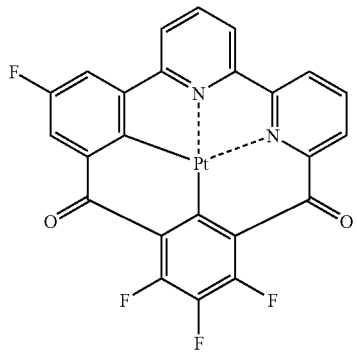
212
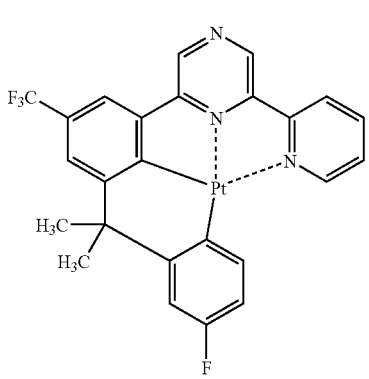
213
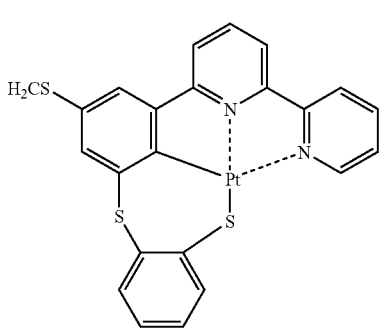
214
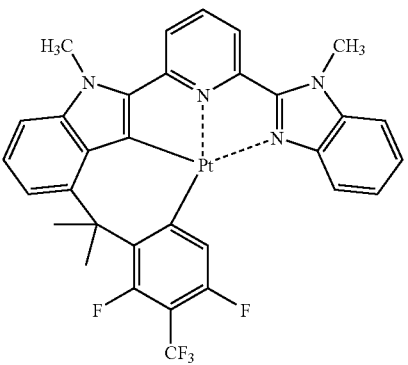
215

-continued
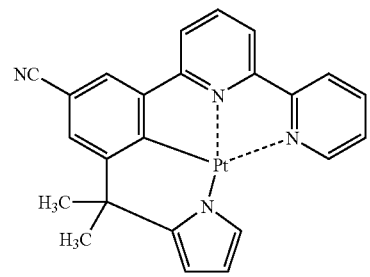
216
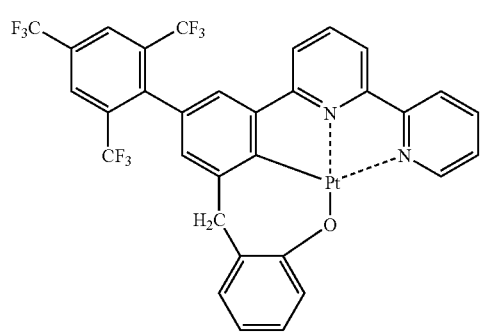
217
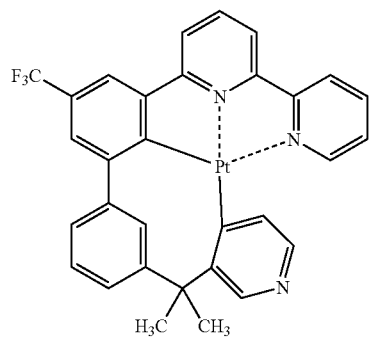
218
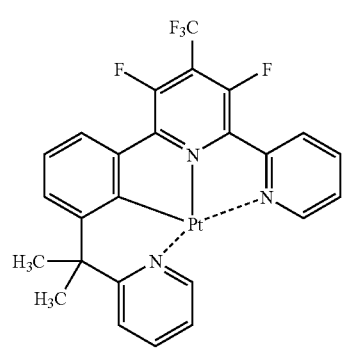
219
-continued
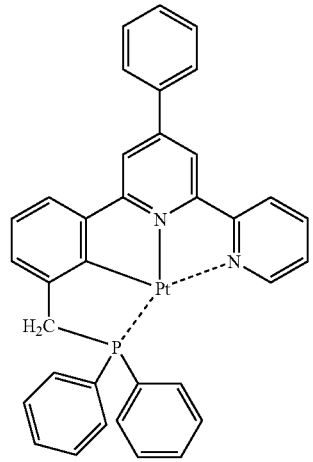
220
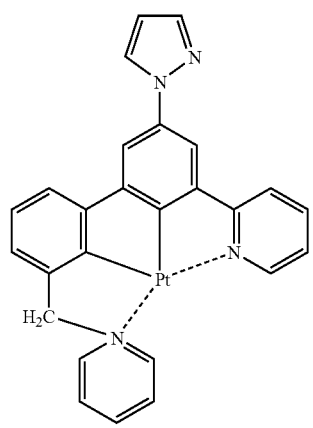
221
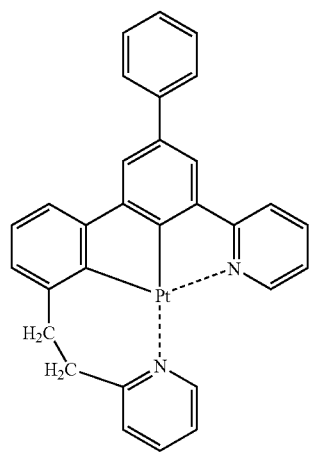
222

-continued
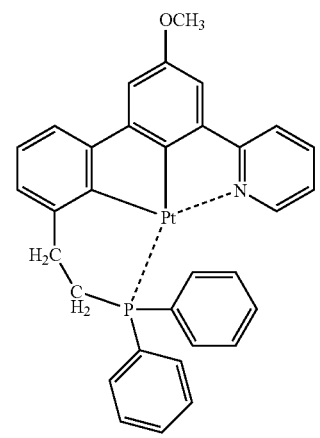
223
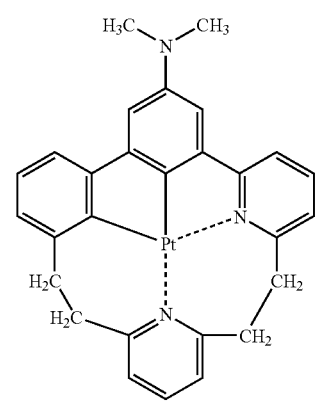
224
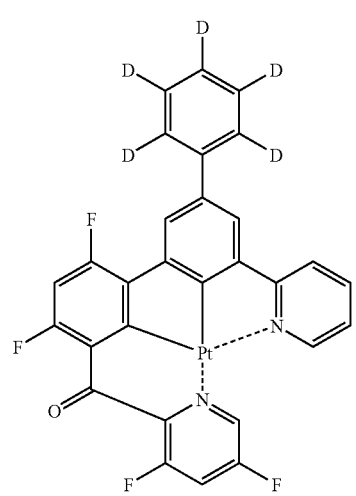
225
-continued
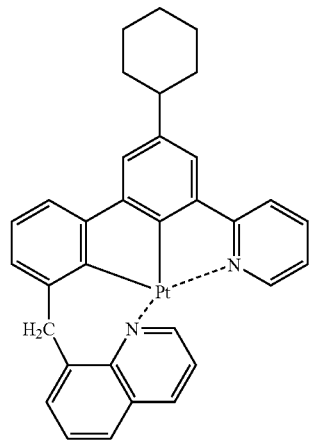
226
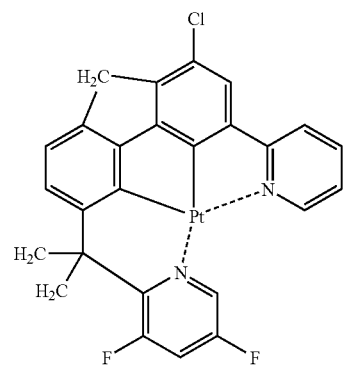
227
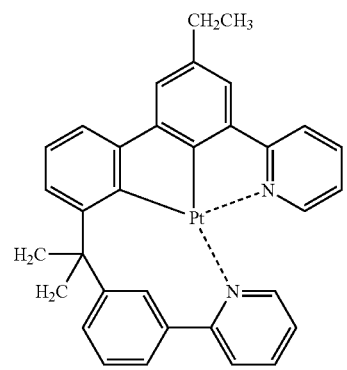
228
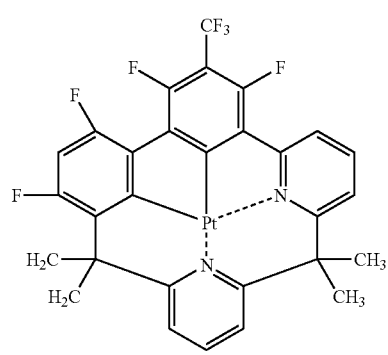
229

-continued
230
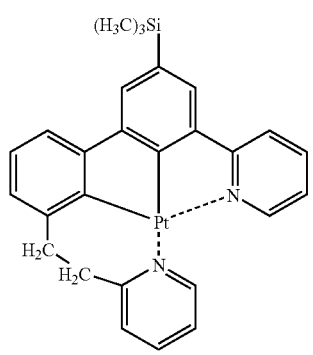
231
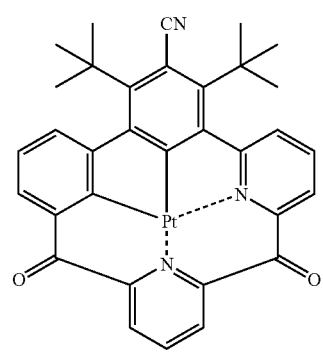
232
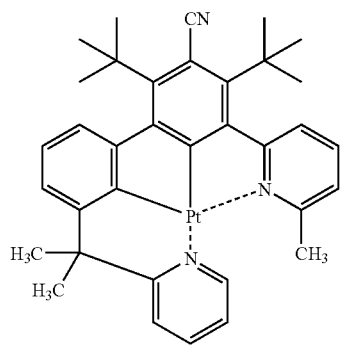
233
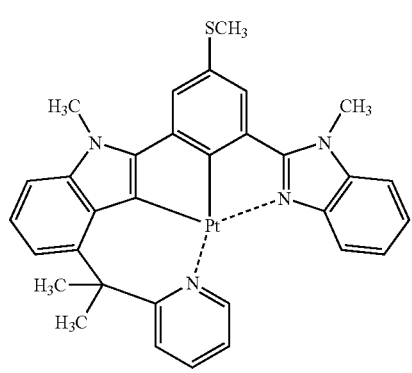
-continued
234
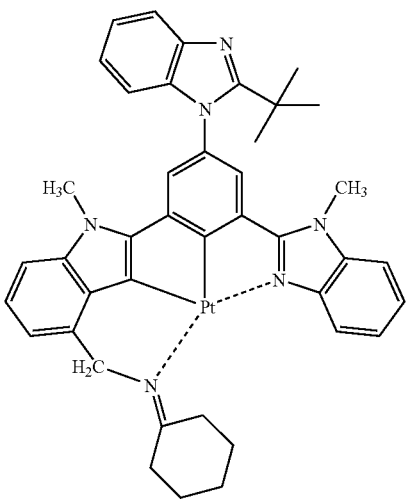
235
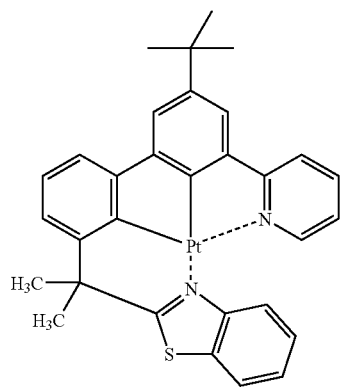
236
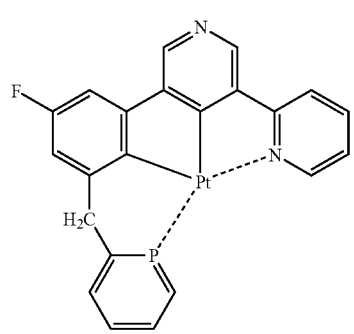
237
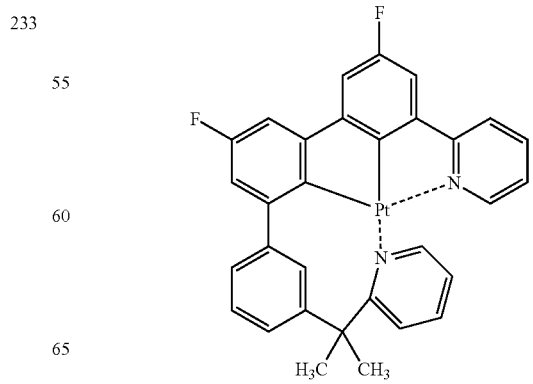

238
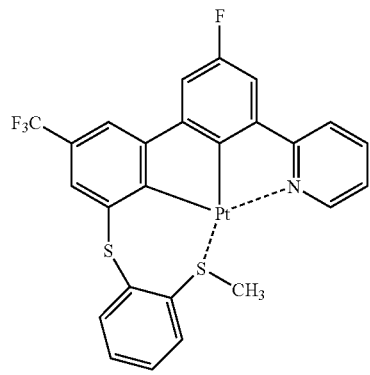
239
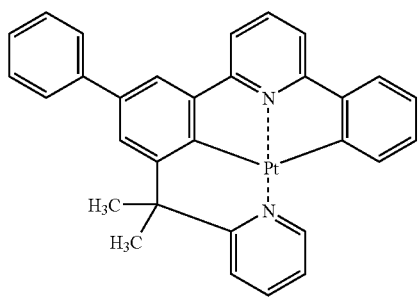
240
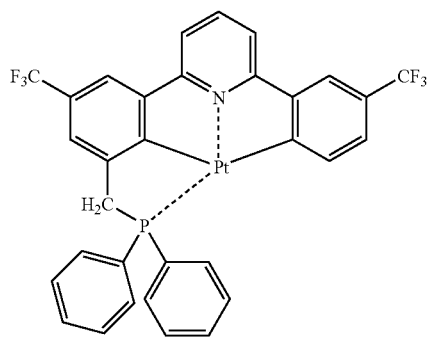
241
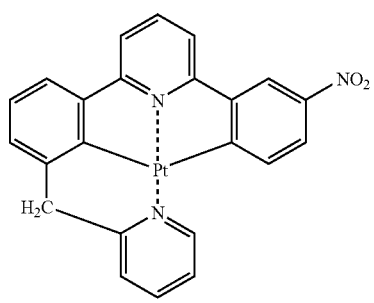
242
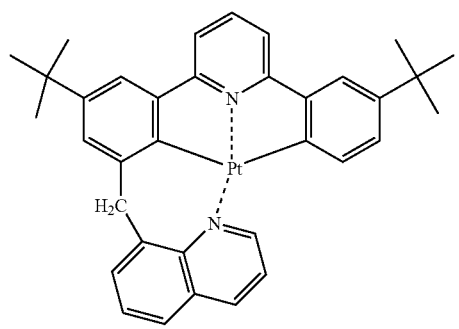
243
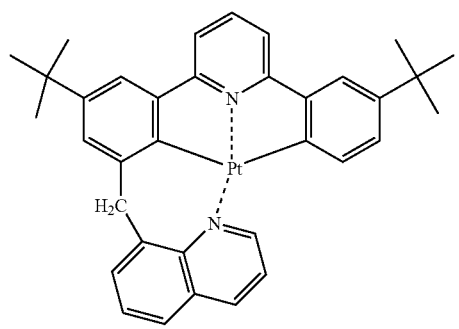
244
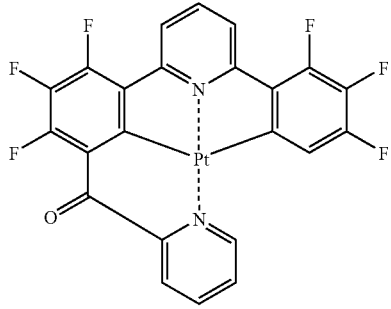
245
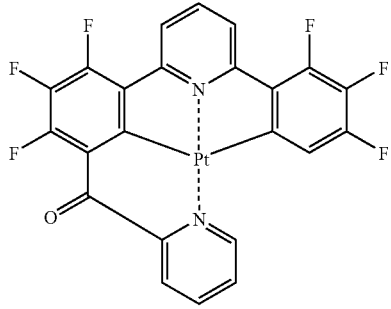

-continued
246
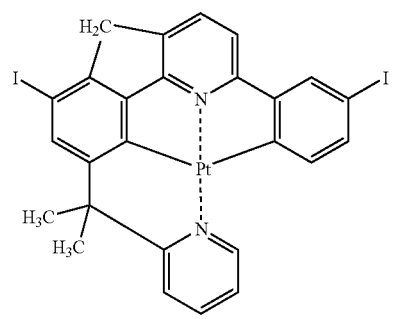
247
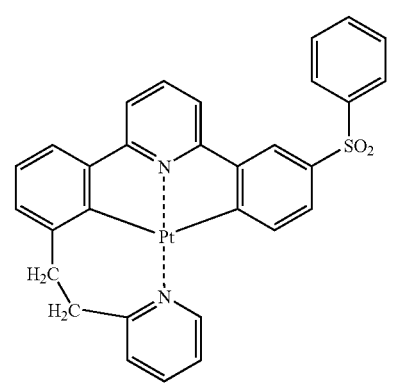
248
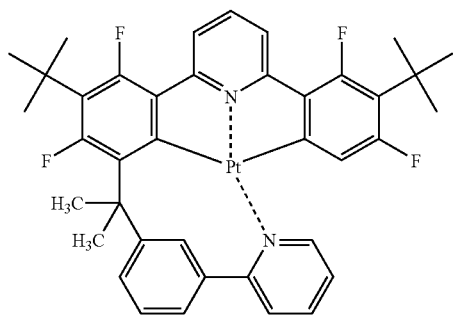
249
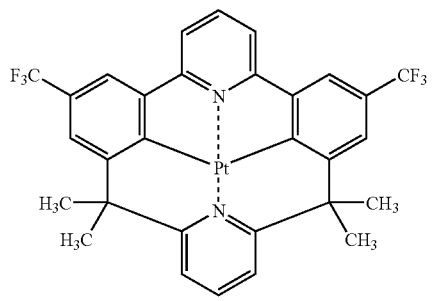
250
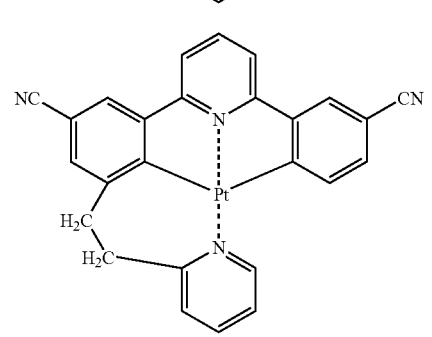
-continued
251
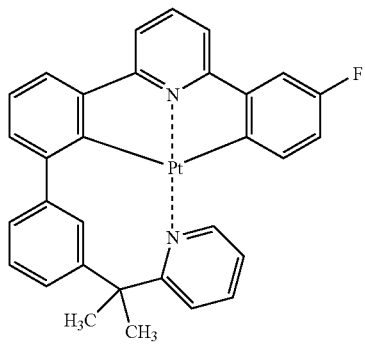
252
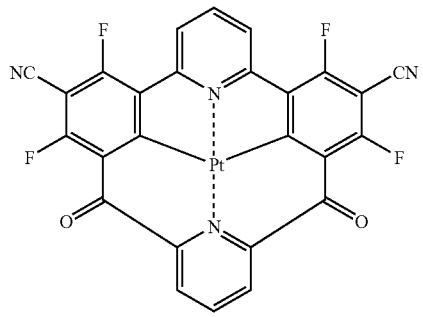
253
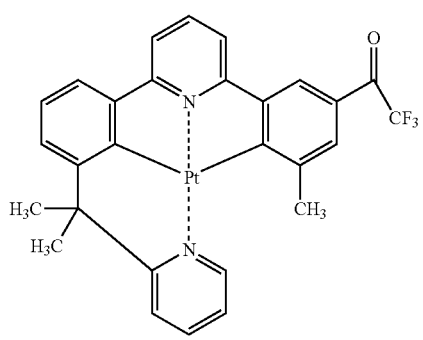
254
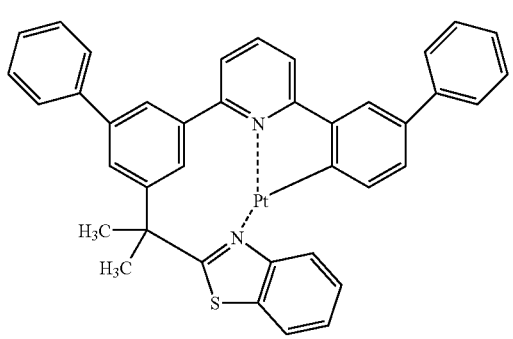

-continued
255
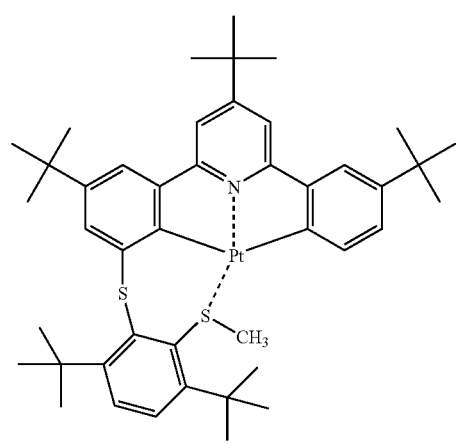
256
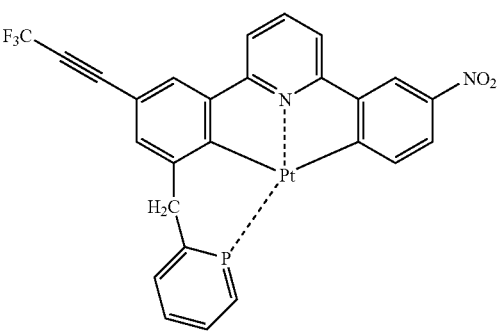
257
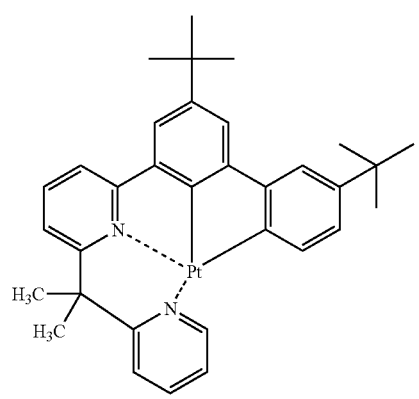
258
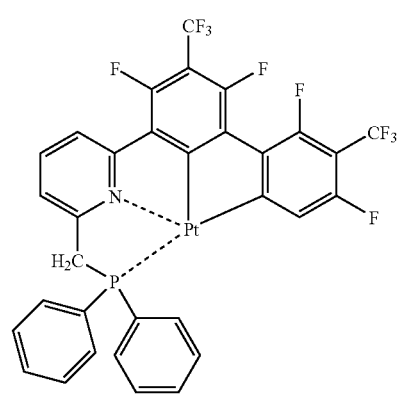
-continued
259
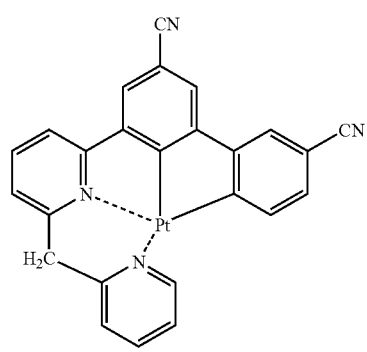
260
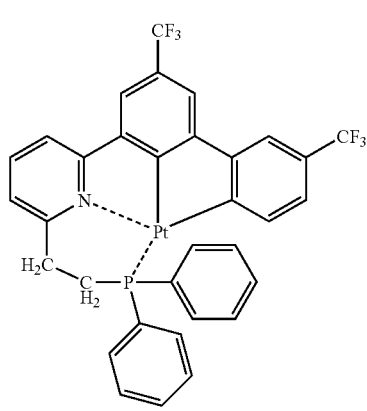
261
262
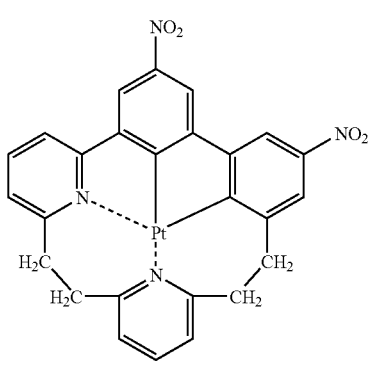

-continued
263
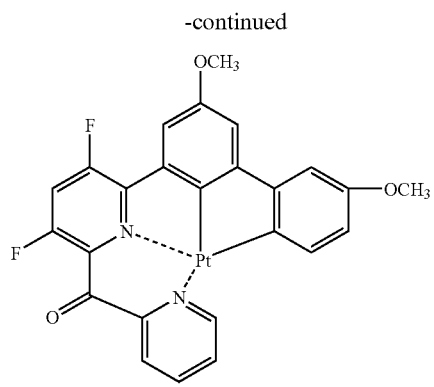
264
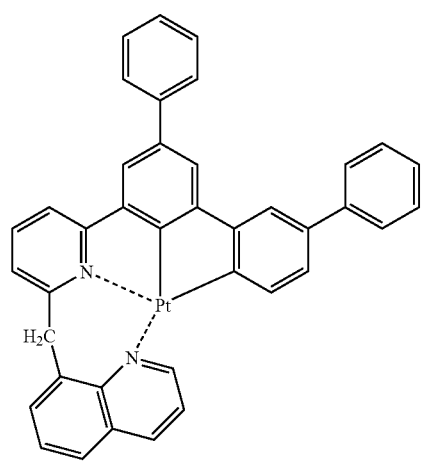
265
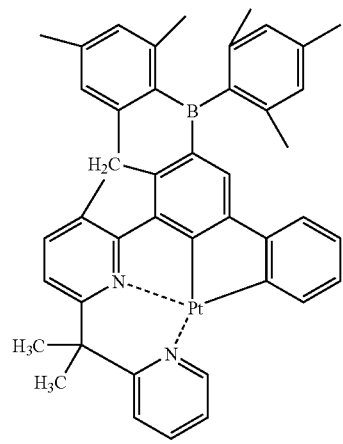
266
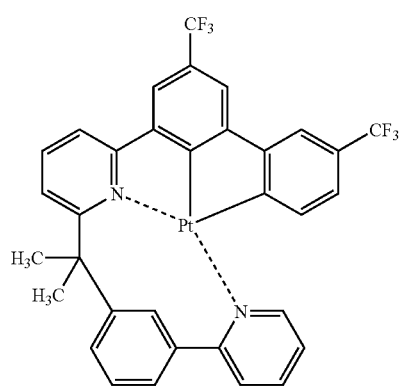
-continued
267
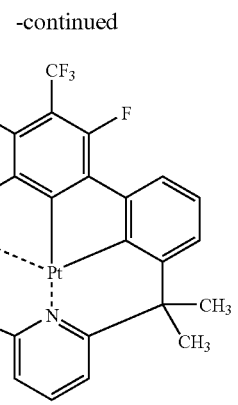
268
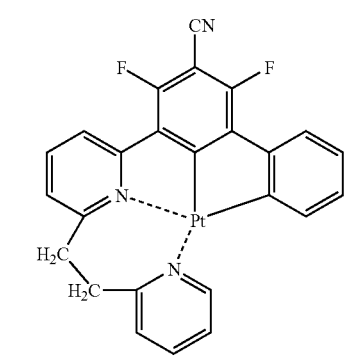
269
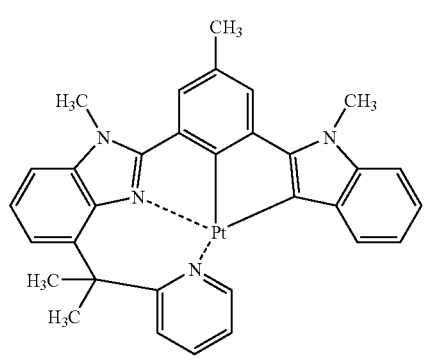
270
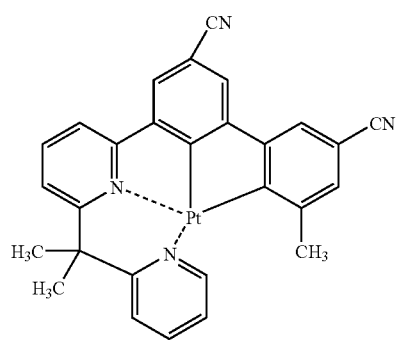

271 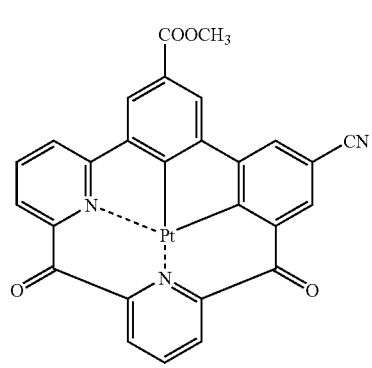
272 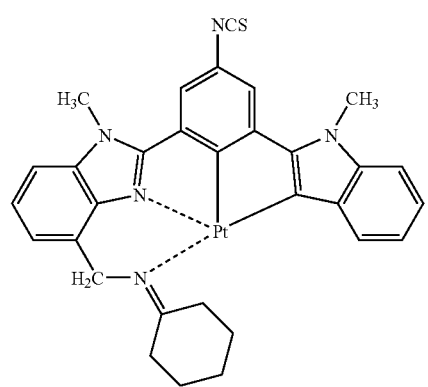
273 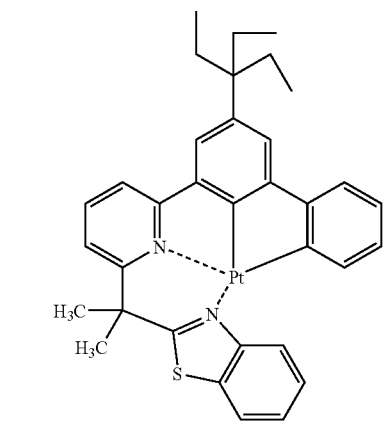
274 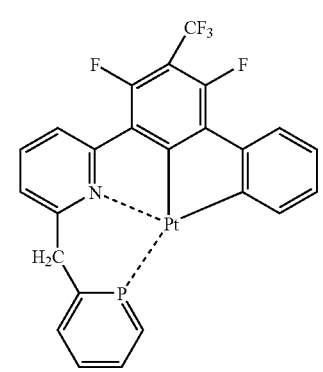
275 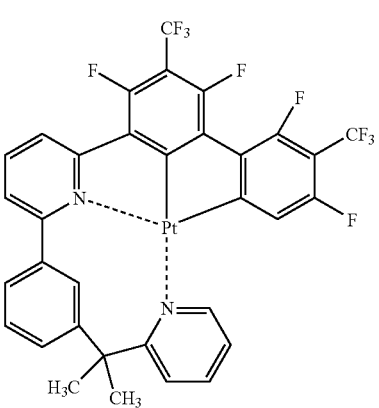
276 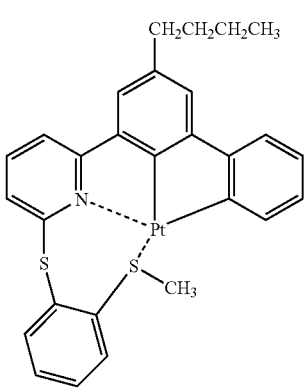
277 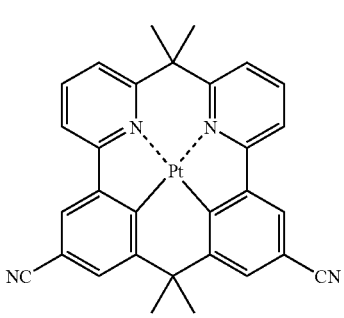
278 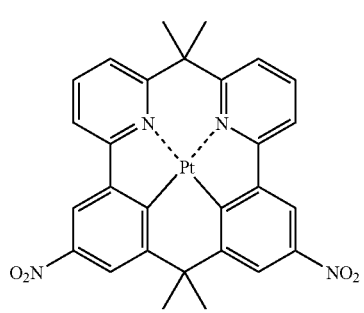

-continued
279
280
281
282
283
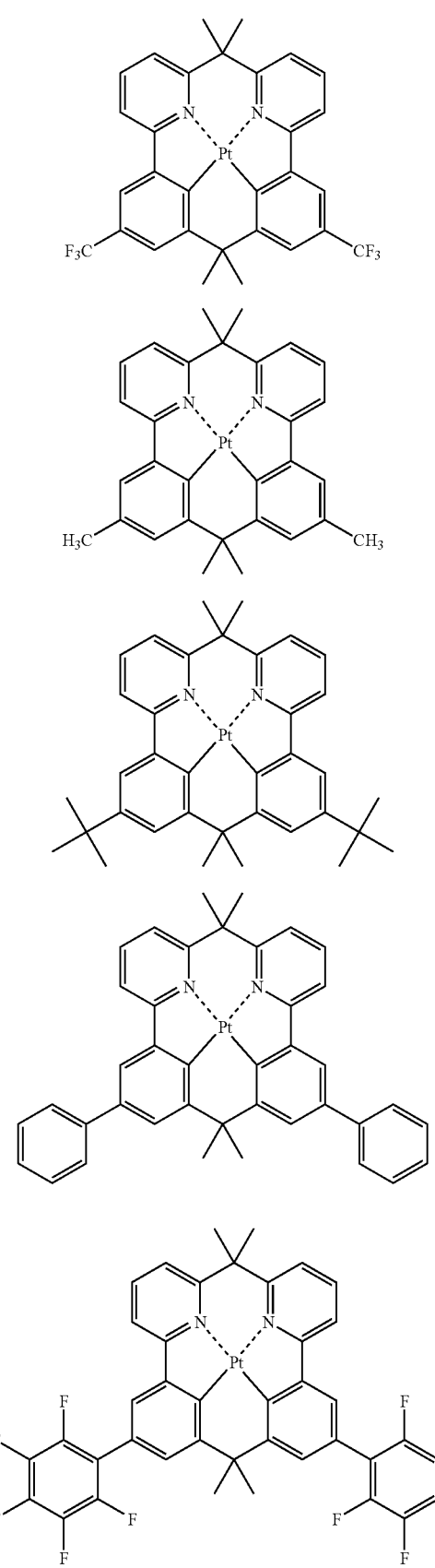
-continued
284
285
286
287
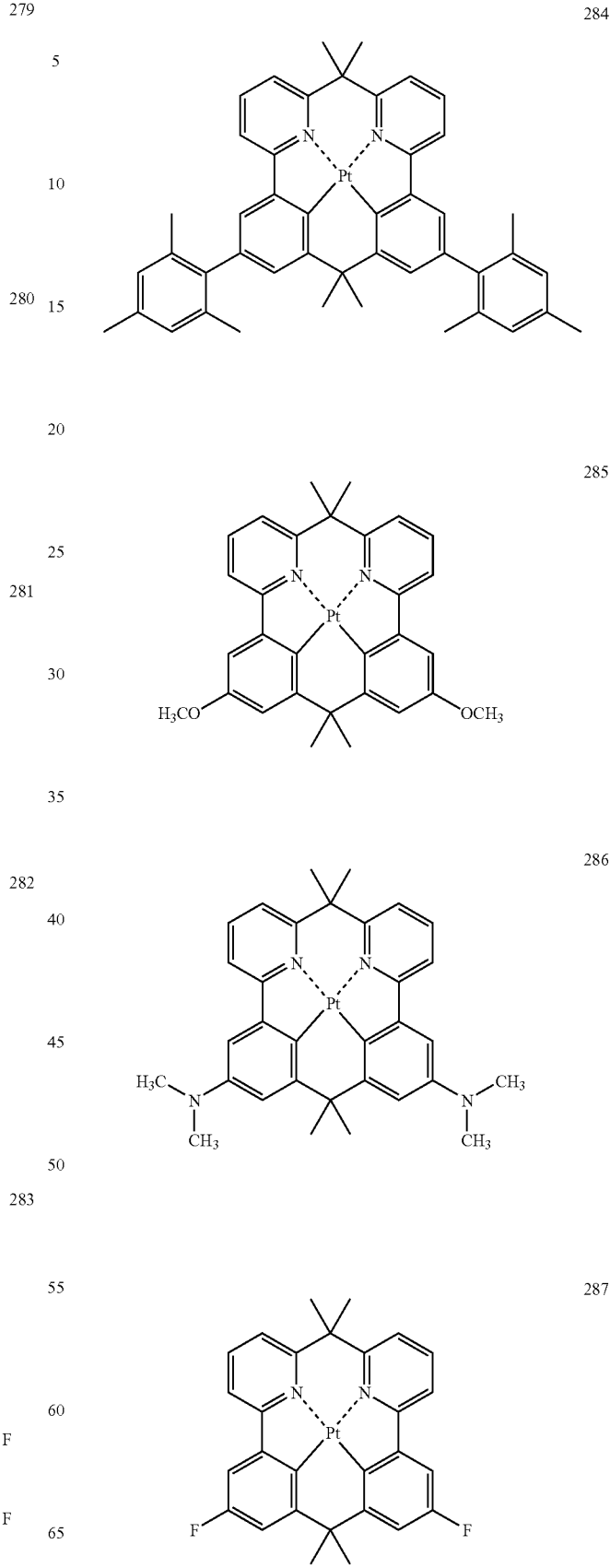

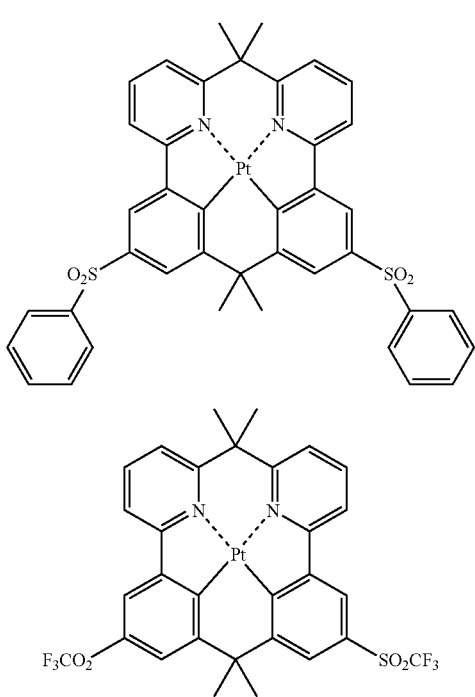

Next, the organic EL device containing the metal complex defined in the present invention will be explained.

The light-emitting device of the present invention may use a usual light-emitting system, driving method and utilization form, except for using the specific platinum complex defined in the present invention.

The specific platinum complex defined in the present invention can be used as any of a hole-injecting material, a hole-transporting material, a light-emitting material, an electron-injecting material, an electron-transporting material, a hole-blocking material, an electron-blocking material, and an exciton-blocking material. Among these, the platinum complex is preferably used as a light-emitting material. When this platinum complex is used as the light-emitting material, it may be used in the case of any of ultraviolet emission, visible light emission and infrared emission, or any of fluorescent light emission or phosphorescent emission. However, it is preferably used for visible light emission and phosphorescent emission.

The formation method of the organic compound layer that can be used in the present invention is not particularly limited, but includes resistance heating vapor deposition method, electrophotographic method, electron beam method, sputtering method, molecular lamination method, coating methods (such as spray coating method, dip coating method, impregnation method, roll coating method, gravure coating method, reverse coating method, roll brushing method, air knife coating method, curtain coating method, spin coating method, flow coating method, bar coating method, micro gravure coating method, air doctor coating method, blade coating method, squeeze coating method, transfer roll coating method, kiss coating method, cast coating method, extrusion coating method, wire bar coating method, and screen coating method), inkjet method, printing method, and transfer method. Among these, the resistance heating vapor deposition method, coating method, and transfer method are preferable from the standpoints of characteristics of devices, and production easiness and cost. When the light-emitting device has a laminating structure having two or more layers, the light-emitting device can be produced by combining the above methods.

In the coating method, the materials may be dissolved or dispersed together with a resin component. As the resin component, there are illustrated, for example, poly(vinyl chloride), polycarbonate, polystyrene, poly(methyl methacrylate), polyester, polysulfone, poly(phenylene oxide), polybutadiene, poly(N-vinylcarbazole), hydrocarbon resin, ketone resin, phenoxy resin, polyamide, ethyl cellulose, vinyl acetate, ABS resin, polyurethane, melamine resin, unsaturated polyester resin, alkyd resin, epoxy resin, and silicone resin.

The light-emitting device of the present invention contains at least one light-emitting layer. The light-emitting device may contain, other than the light-emitting layer, an organic layer, such as a hole-injecting layer, a hole-transporting layer, an electron-injecting layer, an electron-transporting layer and a protective layer. Each of these layers may have other functions. The details of each layer will be explained hereinbelow.

As the materials for the hole-injecting layer and the hole-transporting layer, those materials may be used which have any one of the function of injecting holes from the anode side, the function of transporting holes, and the function of blocking electrons injected from the cathode. Specific examples thereof include, as well as the platinum complex defined in the present invention, carbazole, imidazole, triazole, oxazole, oxadiazole, polyarylalkane, pyrazoline, pyrazolone, phenylenediamine, arylamine, amino-substituted chalcone, styrylanthracene, fluorenone, hydrazone, stilbene, silazane, aromatic tertiary amine compounds, stilylamine, aromatic dimethylidene-series compounds, porphyrin-series compounds, polysilane-series compounds, poly(N-vinylcarbazole), aniline-series copolymers, thiophene oligomers, conductive high molecular oligomers such as polythiophene, organic metal complexes, transition metal complexes, and derivatives thereof.

Thickness of the hole-injecting layer and the hole-transporting layer is not particularly limited, but is preferably 1 mm to 5 µm, more preferably 5 nm to 1 µm, and still more preferably 10 nm to 500 nm. The hole-transporting layer may be of a single layer structure composed of one or more of the above-described materials, or may be of a multi-layer structure composed of a plurality of layers having the same composition or different compositions.

Materials for the electron-injecting layer and the electron-transporting layer may be any, as long as they have any of the function of injecting electrons from the cathode, the function of transferring electrons and the function of blocking holes injected from the anode. Specific examples thereof include triazole, triazine, oxazole, oxadiazole, fluorenone, anthraquinodimethane, anthrone, diphenylquinone, thiopyran dioxide, carbodiimide, fluorenylidenemethane, distyrylpyrazine, silole, tetracarboxylic acid anhydrides of aromatic rings such as naphthalene and perylene, phthalocyanine, various metal complexes represented by metal complexes of 8-quinolinol derivatives, metallophthalocyanine, metal complexes each having benzoxazole or benzothiazole as a ligand, and derivatives of these compounds, as well as the platinum complex defined in the present invention.

Thickness of the electron-injecting layer and the electron-transporting layer is not particularly limited, but is preferably 1 nm to 5 µm, more preferably 5 nm to 1 µm, and still more preferably 10 nm to 500 nm. The electron-injecting layer and the electron-transporting layer may be of a single layer structure composed of one or more of the above-described materials, or may be of a multi-layer structure composed of a plurality of layers having the same composition or different compositions.

Materials of the light-emitting layer may be any, as long as they have the function of receiving holes from the anode, the hole-injecting layer, the hole-transporting layer or the like at the time of voltage application, and they have also any of the function of receiving electrons from the cathode, the electron-injecting layer, the electron-transporting layer or the like, the function of transporting injected charges, the function of providing the field of recombination of holes with electrons to form excitons, the function of transferring excited energy, and the function of emitting light from excitons. Examples of the materials used in the light-emitting layer include, as well as the platinum complex defined in the present invention, benzoxazole, benzimidazole, benzothiazole, styrylbenzene, polyphenyl, diphenylbutadiene, tetraphenylbutadiene, naphthalimide, coumarin, perylene, perynone, oxadiazole, aldazine, pyralidine, cyclopentadiene, bis(styryl)anthracene, quinacridone, pyrrolopyridine, thiadiazolopyridine, styrylamine, aromatic dimethylidyne compounds, polymer compounds such as polythiophene, polyphenylene and polyphenylenevinylene, carbazole, imidazole, triazole, oxazole, oxadiazole, polyarylalkane, pyrazoline, pyrazolone, phenylenediamine, arylamine, amino-substituted chalcone, styrylanthracene, fluorenone, hydrazone, stilbene, silazane, aromatic tertiary amine compounds, styrylamine, aromatic dimethylidene compounds, porphyrin-type compounds, polysilane-type compounds, poly(N-vinylcarbazole), conductive high-molecular oligomers such as aniline-type copolymers, thiophene oligomer and polythiophene, various metal complexes represented by organic metal complexes, transition metal complexes, metal complexes of triazole, triazine, oxazole, oxadiazole, fluorenone, anthraquinonedimethane, anthrone, diphenylquinone, thiopyran dioxide, carbodiimide, fluorenylidenemethane, distyrylpyrazine, silol, aromatic cyclic tetracarboxylic acid anhydrides such as naphthalene and perylene, phthalocyanine and 8-quinolinol derivative, metal phthalocyanine, and metal complexes each having benzoxazole or benzothiazole as a ligand, and derivatives of the above compounds.

The light-emitting layer may be of a single layer or a multi-layer composed of a plurality of layers. When the light-emitting layer is made of a plurality of layers, each layer may emit light having a different color. Even when the light-emitting layer is constituted of a plurality of layers, each layer is preferably constituted only of a phosphorescent material and a metal complex. Although there is no particular limitation on the thickness of the light-emitting layer, it is usually preferably from 1 nm to 5 µM, more preferably from 5 nm to 1 µm, and further preferably from 10 nm to 500 nm.

As materials for the protective layer, any material may be used that can prevent substances capable of accelerating deterioration of the device, such as moisture or oxygen, from invading into the device. Specific examples thereof include metals, e.g. In, Sn, Pb, Au, Cu, Ag, Al, Ti, and Ni; metal oxides, e.g. MgO, SiO, $SiO_2$, $Al_2O_3$, GeO, NiO, CaO, BaO, $Fe_2O_3$, $Y_2O_3$, and $TiO_2$; metal fluorides, e.g. $MgF_2$, LiF, $AlF_3$, and $CaF_2$; polyethylene, polypropylene, poly(methyl methacrylate), polyimide, polyurea, polytetrafluoroethylene, polychlorotrifluoroethylene, polydichlorodifluoroethylene, a copolymer of chlorotrifluoroethylene and dichlorodifluoroethylene, a copolymer obtained by copolymerizing a monomer mixture containing at least one comonomer and tetrafluoroethylene, a fluorine-containing copolymer having a cyclic structure in the main chain of the copolymer, a water-absorbing substance showing a water absorption of 1% or more, and a moisture barrier substance showing a water absorption of 0.1% or less.

A method for forming the protective layer is not particularly limited, and use may be made, for example, of a vacuum deposition method, a sputtering method, a reactive sputtering method, an MBE (molecular beam epitaxy) method, a cluster ion beam method, an ion plating method, a plasma polymerization method (high frequency-excited ion plating method), a plasma CVD (chemical vapor deposition) method, a laser CVD method, a heat CVD method, a gas source CVD method, a coating method, an inkjet method, a printing method, a transfer method, or an electrophotographic method.

The anode, supplying holes to the hole-injecting layer, the hole-transporting layer, the light-emitting layer and the like, can be formed of metals, alloys, metal oxides, electric conductive compounds, mixtures thereof, and the like, preferably materials having a work function of 4 eV or more. Specific examples thereof include conductive metal oxides such as tin oxide, zinc oxide, indium oxide, indium tin oxide (ITO), and the like; metals such as gold, silver, chromium, nickel, and the like; further mixtures or laminates of the metals with the conductive metal oxides; inorganic conductive materials such as copper iodide, copper sulfide, and the like; organic conductive materials such as polyaniline, polythiophene, polypyrrole, and the like; and mixtures or laminates thereof with ITO. Conductive metal oxides are preferred, and ITO is particularly preferred in terms of productivity, high conductivity, and transparency.

The thickness of the anode may be appropriately selected depending on the kind of the material, preferably from 10 nm to 5 nm, more preferably from 50 nm to 1 µm, and further preferably from 100 nm to 500 nm.

As the anode, one in which layer formation is carried out on soda-lime glass, non-alkali glass, or a transparent resin substrate is usually used. When glass is used, non-alkali glass is preferably used for decreasing ions eluted from glass. When soda-lime glass is used, it is preferable to use one provided with a barrier coat of silica or the like. There is no particular limitation on the thickness of the substrate, as long as it is sufficient to keep its mechanical strength. When glass is used, the thickness is usually 0.2 mm or more, and preferably 0.7 mm or more. Various methods are used for the preparation of the anodes depending on the kind of the material. For example, in case of ITO, film formation may be carried out by a method such as electron beam method, sputtering method, resistance heating vapor deposition method, ion plating method, chemical reaction method (e.g., sol-gel method), spraying method, dipping method, heat CVD method, plasma CVD, coating of a dispersion of ITO, and the like. According to treatments of the anode such as washing and others, the driving voltage for the device may be reduced and the luminous efficiency may be raised. For example, in a case of ITO, UV-ozone treatment, plasma treatment and the like are effective.

The cathode supplies electrons to the electron-injecting layer, the electron-transporting layer, the light-emitting layer and the like. The material for the cathode may be selected considering ionization potential, stability, and adhesion to layers adjacent to the cathode, such as the electron-injecting layer, the electron-transporting layer, and the light-emitting layer. As the material for the cathode, metals, alloys, metal oxides, electric conductive compounds, or mixtures thereof may be used. Specific examples thereof include alkali metals (for example, Li, Na, K and Cs) or fluorides thereof, alkali earth metals (for example, Mg and Ca) or fluorides thereof, gold, silver, lead, aluminum, sodium-potassium alloys or mixed metals thereof, lithium-aluminum alloys or mixed metals thereof, magnesium-silver alloys or mixed metals thereof, and rare earth metals such as indium and ytterbium. Materials having a work function of 4 eV or less are preferred, more preferably aluminum, lithium-aluminum alloys or mixed metals thereof, magnesium-silver alloys or mixed metals thereof, or the like.

The film thickness of the cathode can be appropriately selected depending on the material, and is preferably from 10 nm to 5 µm, more preferably from 50 nm to 1 µm, and further preferably from 100 nm to 1 µm.

For the preparation of the cathode, methods such as electron beam method, sputtering method, resistance heating vapor deposition method, and coating method may be used. The metals may be vapor deposited as simple substances, or two or more components may be vapor deposited at the same time. Further, it is also possible to vapor deposit a plurality of metals at the same time to form an alloy electrode, or an alloy previously prepared may also vapor deposited.

The anode and the cathode with low sheet resistance are preferable, and those with several-hundred $\Omega/\square$ or less are more preferable.

The light-extraction efficiency in the light-emitting device of the present invention can be improved by various known techniques. For example, surface structuring of the substrate (for example, formation of a fine concavo-convex pattern), controlling the refractive index of the substrate, ITO layer, or organic layer(s), and controlling the thickness of the substrate, ITO layer, or organic layer(s), can be included. These improvements can lead to increase light-extraction efficiency and external quantum efficiency.

The external quantum efficiency of the light-emitting device of the present invention is preferably 5% or more, more preferably 10% or more, and still more preferably 15% or more. As the value of the external quantum efficiency, the maximum value of the external quantum efficiency when the device is driven at 25° C. or the value of the external quantum efficiency at a luminance close to 100 to 2,000 cd/m² when the device is driven at 25° C. can be used.

The light-emitting device of the present invention may be of a so-called top emission type, in which light is emitted from the anode side of the device.

Examples of the substrate material used for the light-emitting device of the present invention, is not particularly limited, include inorganic materials such as zirconia-stabilized yttrium, glass and the like; and macromolecular (high molecular) materials such as polyesters (for example, polyethylene terephthalate, polybutylene terephthalate, and polyethylene naphthalate), polyethylenes, polycarbonates, polyethersulfones, polyarylates, allyldiglycolcarbonates, polyimides, polycycloolefins, norbornene resins, poly(chlorotrifluoroethylene), Teflon (registered trade mark), and polytetrafluoroethylene-polyethylene copolymers.

The light-emitting layer of the organic electroluminescence device of the present invention may have at least one layered structure. The number of layers in this layered structure is preferably from 2 to 50, more preferably from 4 to 30, and further preferably from 6 to 20.

The thickness of each of the layers constituting the layered structure is not particularly limited, but it is preferably from 0.2 to 20 nm, more preferably from 0.4 to 15 nm, even more preferably from 0.5 to 10 nm, and particularly preferably from 1 to 5 nm.

The light-emitting layer of the organic electroluminescence device of the present invention may have plural domain structures. The light-emitting layer may contain therein some other domain structure. The diameter of each of the domain structures is preferably from 0.2 to 10 nm, more preferably from 0.3 to 5 nm, even more preferably from 0.5 to 3 nm, and particularly preferably from 0.7 to 2 nm.

The organic EL device of the present invention can be preferably used for display devices, displays, back light, electrophotography, light source for lighting equipment, recording, light-exposure or reading, indicator, signboard, interior and optical communication.

According to the present invention, it is possible to provide a light-emitting device having high luminance, high luminous efficiency and high durability. Further, according to the present invention, it is possible to provide a metal complex compound preferable to provide the light-emitting device.

The present invention can provide an organic EL device in which a platinum complex having a cyclic or non-cyclic quadridentate ligand and a substituent at the para-position of a phenyl group bonded to the platinum is contained in an organic layer.

The light-emitting device of the present invention has high luminance and high external quantum efficiency, and it is excellent in durability. Also, the platinum complex compound defined in the present invention is preferable to provide the excellent light-emitting device as mentioned above.

The present invention will be described in more detail based on the following examples, but the invention is not intended to be limited thereto.

EXAMPLES

Synthetic Examples

Synthesis of the Exemplified Compound 24

The ligand 24 could be synthesized using known methods described in documents, and was synthesized using SM as a starting material (see Journal of Organic Chemistry, 53, 786-790 (1988)) by known organic synthetic methods.

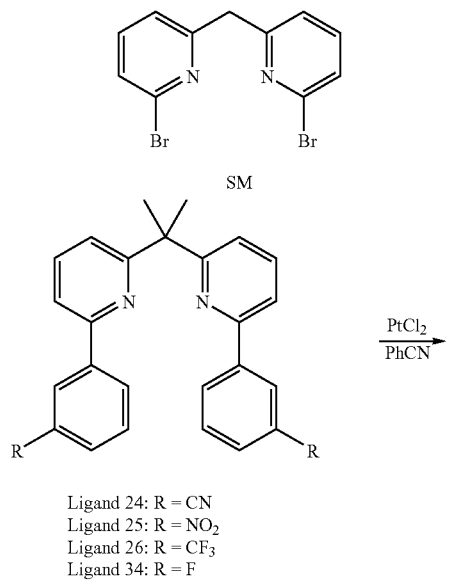

Ligand 24: R = CN
Ligand 25: R = NO$_2$
Ligand 26: R = CF$_3$
Ligand 34: R = F

-continued

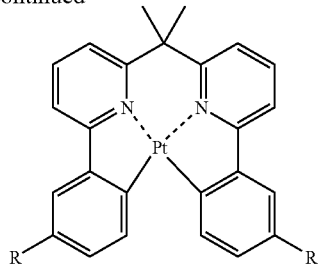

Exemplified compound 24: R = CN
Exemplified compound 25: R = NO$_2$
Exemplified compound 26: R = CF$_3$
Exemplified compound 34: R = F Under a nitrogen flow, 235 mg of the ligand 24 and 156 mg of platinous chloride were suspended in 10 mL of benzonitrile, and the mixture was raised up to 200° C. and heated for 2 hours. The reaction mixture was cooled to a room temperature, to obtain precipitates. These precipitates were collected by filtration and then purified by using a silica gel column (eluent: chloroform), to obtain 189 mg of the exemplified compound 24 (yield: 54%).

Synthesis of the Exemplified Compound 25

The ligand 25 could be synthesized using known methods described in documents, and was synthesized using SM as a starting material by known organic synthetic methods.

Under a nitrogen flow, 175 mg of the ligand 25 and 105 mg of platinous chloride were suspended in 10 mL of benzonitrile, and the mixture was raised up to 200° C. and heated for 2 hours. The reaction mixture was cooled to a room temperature, and a small amount of hexane was then added to the mixture, to obtain precipitates. These precipitates were collected by filtration and then purified by using a silica gel column (eluent: chloroform), to obtain 155 mg of the exemplified compound 25 (yield: 61%).

Synthesis of the Exemplified Compound 26

The ligand 26 could be synthesized using known methods described in documents, and was synthesized using SM as a starting material by known organic synthetic methods.

Under a nitrogen flow, 800 mg of the ligand 26 and 437 mg of platinous chloride were suspended in 20 mL of benzonitrile, and the mixture was raised up to 200° C. and heated for 2 hours. The reaction mixture was cooled to a room temperature, and a small amount of hexane was then added to the mixture, to obtain precipitates. These precipitates were collected by filtration and then purified by using a silica gel column (eluent: chloroform), to obtain 501 mg of the exemplified compound 26 (yield: 45%).

Synthesis of the Exemplified Compound 34

The ligand 34 could be synthesized using known methods described in documents, and was synthesized using SM as a starting material by known organic synthetic methods.

Under a nitrogen flow, 340 mg of the ligand 34 and 234 mg of platinous chloride were suspended in 15 mL of benzonitrile, and the mixture was raised up to 200° C. and heated for 2 hours. The reaction mixture was cooled to a room temperature, and a small amount of hexane was then added to the mixture, to obtain precipitates. These precipitates were collected by filtration and then purified by using a silica gel column (eluent: chloroform), to obtain 25 mg of the exemplified compound 34 (yield: 5%).

Organic EL Device

Comparative Example 1

A cleaned ITO substrate was placed in a vacuum deposition apparatus, and NPD was vacuum-deposited thereon in a thickness of 50 nm. Further, CBP and Ir(ppy)$_3$ were vacuum-deposited thereon in a thickness of 40 nm with a mass ratio of 10:1, and BAlq was vacuum-deposited thereon in a thickness of 10 nm, and, further, Alq was vacuum-deposited thereon in a thickness of 30 nm. On the thus-obtained organic thin film, a patterned mask (light-emitting area: 4 mm×5 mm) was provided. After vacuum-depositing lithium fluoride in a thickness of 3 nm, aluminum was vacuum-deposited thereon in a thickness of 60 nm, to prepare an organic EL device of the comparative example 1. When a direct current constant voltage was applied to the thus-obtained organic EL device, green color emission having an emission maximum wavelength $\lambda_{max}$ of 514 nm was observed, and the external quantum efficiency of the organic EL device was 6.4%.

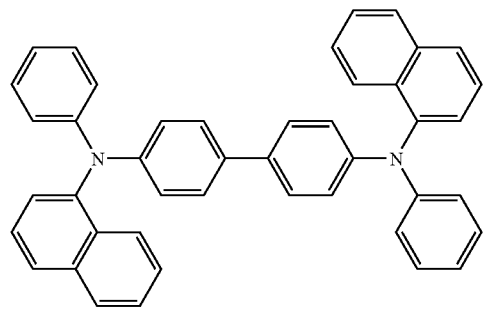

NPD

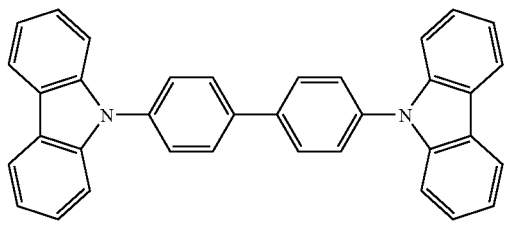

CBP

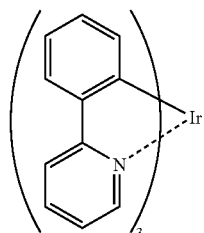

Ir(ppy)$_3$

-continued

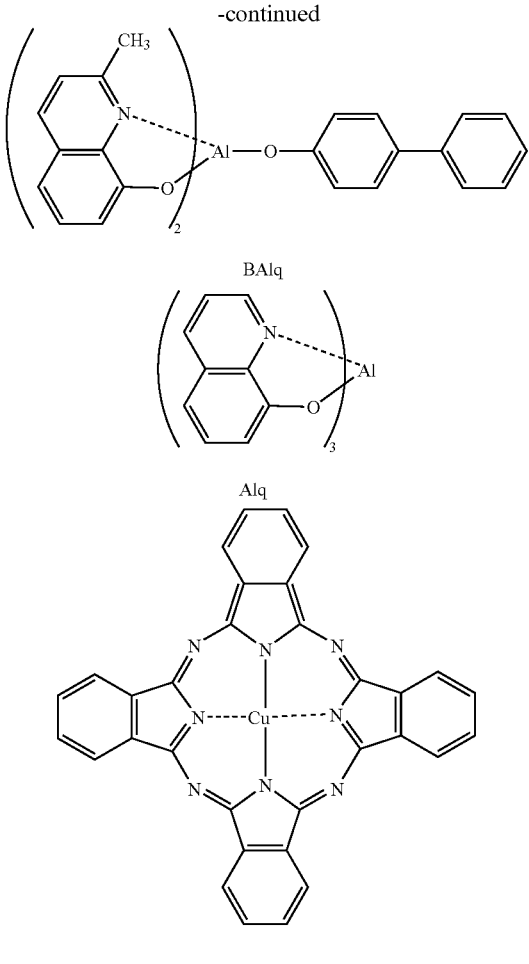

BAlq

Alq

CuPC

Example 1

An organic EL device of this invention 1 was prepared in the same manner as in the comparative example 1, except that the exemplified compound 24 was used in place of Ir(ppy)$_3$. When a direct current constant voltage was applied to the thus-obtained organic EL device, bluish green emission having an emission maximum wavelength $\lambda_{max}$ of 500 nm was observed, and the external quantum efficiency of the EL device was 13.0%.

Example 2

The devices prepared in the comparative example 1 and the example 1 were continuously driven at an initial luminescence of 500 cd/m$^2$. As a result, while the luminance half time of the device of the comparative example 1 was 85 hours, the luminance half time of the device of the example 1 was 800 hours.

It is apparent from the above examples that an organic EL device having high luminous efficiency and highly durability can be obtained by using the compound defined in the present invention.

Having described our invention as related to the present embodiments, it is our intention that the invention not be limited by any of the details of the description, unless otherwise specified, but rather be construed broadly within its spirit and scope as set out in the accompanying claims.

What we claim is:

1. A compound represented by the formula (V):

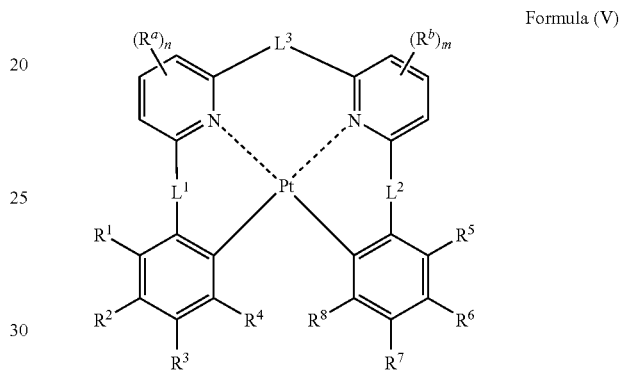

Formula (V)

wherein $L^1$, $L^2$ and $L^3$ each independently represent a single bond or a linking group; $R^1$, $R^3$, $R^4$, $R^5$, $R^7$ and $R^8$ each independently represent a hydrogen atom or a substituent; wherein $R^2$ and $R^6$ each independently represent an alkyl group, an aryl group, an amino group, an aryloxy group, a heterocyclic oxy group, an acyl group, an alkoxycarbonyl group, an aryloxycarbonyl group, an alkylthio group, an arylthio group, a heterocyclicthio group, a sulfonyl group, a halogen group, a cyano group, a heterocyclic group, a silyl group or a silyloxy group; $R^a$ and $R^b$ each independently represent a hydrogen atom, an alkyl group, an aryl group, an amino group, an alkoxy group or a fluorine atom; and n and m each independently represent an integer of from 0 to 3.

2. A compound according to claim 1, wherein $R^2$ and $R^6$ each independently represent an alkyl group, an aryl group, a sulfonyl group, a fluorine atom, a cyano group, or a heterocyclic group; and $R^a$ and $R^b$ each independently represent a hydrogen atom, an alkyl group, an aryl group, an amino group, an alkoxy group or a fluorine atom.

* * * * *